United States Patent
Omichi et al.

(10) Patent No.: US 9,488,606 B2
(45) Date of Patent: Nov. 8, 2016

(54) METHOD FOR DETECTING NON-SUPERCONDUCTING TRANSITION OF SUPERCONDUCTING WIRE

(71) Applicant: Fujikura Ltd., Kohtoh-ku, Tokyo (JP)

(72) Inventors: Koji Omichi, Sakura (JP); Yoshihiro Terada, Sakura (JP)

(73) Assignee: FUJIKURA LTD., Tokyo (JP)

( * ) Notice: Subject to any disclaimer, the term of this patent is extended or adjusted under 35 U.S.C. 154(b) by 1145 days.

(21) Appl. No.: 13/728,570

(22) Filed: Dec. 27, 2012

(65) Prior Publication Data
US 2016/0047763 A1 Feb. 18, 2016

Related U.S. Application Data

(63) Continuation of application No. PCT/JP2011/058700, filed on Apr. 6, 2011.

(30) Foreign Application Priority Data

Jun. 28, 2010 (JP) ................................. 2010-146304
Mar. 16, 2011 (JP) ................................. 2011-057939

(51) Int. Cl.
*G01N 1/14* (2006.01)
*G01N 13/00* (2006.01)
(Continued)

(52) U.S. Cl.
CPC ............... *G01N 25/00* (2013.01); *G01K 1/14* (2013.01); *G01K 3/005* (2013.01); *G01K 11/3206* (2013.01); *G01K 13/006* (2013.01); *G01K 2203/00* (2013.01)

(58) Field of Classification Search
CPC ................................................ G01K 11/3206
USPC ........................................................ 374/161
See application file for complete search history.

(56) References Cited

U.S. PATENT DOCUMENTS 5,126,655 A 6/1992 Kita et al.
6,072,922 A 6/2000 Albin et al.
(Continued)

FOREIGN PATENT DOCUMENTS

CN 1963477 A 5/2007
CN 101126787 A * 2/2008
(Continued)

OTHER PUBLICATIONS

Joo et al ("Development of Quench Detection Method Based on Normal Transition Behaviors for HTS Coils" IEEE Transactions on Applied Superconductivity, Jul. 17, 2009, vol. 19 , Issue: 3).*
Bai et al ("Quench Propagation properties analysis of high-temperature superconductors using finite element method", Physica C #436, 2006, p. 99-102).*
(Continued)

*Primary Examiner* — Minh Phan
*Assistant Examiner* — Leon W Rhodes, Jr.
(74) *Attorney, Agent, or Firm* — Sughrue Mion, PLLC

(57) ABSTRACT

A method for detecting a non-superconducting transition of a superconducting wire including a substrate, a superconducting layer having a critical temperature of 77 K or more, and a metal stabilization layer includes, adhesively attaching an optical fiber where a plurality of fiber Bragg gratings are formed in a core along a longitudinal direction thereof to the superconducting wire; measuring in advance a Bragg wavelength shift of the fiber Bragg gratings for a temperature variation of the superconducting wire, and determining a relational expression based on the shift for a temperature calculation of the superconducting wire; determining temperature variations of the fiber Bragg gratings before and after the non-superconducting transition of the superconducting wire using the relational expression; and calculating a propagation rate of the non-superconducting transition based on both a time difference of temperature increases of the fiber Bragg gratings, and an interval between each of the fiber Bragg gratings.

17 Claims, 12 Drawing Sheets

(51) Int. Cl.
   *G01N 25/00* (2006.01)
   *G01K 1/14* (2006.01)
   *G01K 3/00* (2006.01)
   *G01K 11/32* (2006.01)
   *G01K 13/00* (2006.01)

(56) References Cited

U.S. PATENT DOCUMENTS

2001/0019103 A1* 9/2001 Sugai .................... G01L 1/246
                                                         250/227.18
2009/0202194 A1* 8/2009 Bosselmann ...... G01K 11/3206
                                                         385/12

FOREIGN PATENT DOCUMENTS

| CN | 102305804 A | 1/2012 |
| JP | 5299245 A | 11/1993 |
| JP | 7-170721 A | 7/1995 |
| JP | 8-304271 A | 11/1996 |
| JP | 2577682 B2 | 2/1997 |
| JP | 11162269 A | 6/1999 |

OTHER PUBLICATIONS

Communication dated Jul. 3, 2015, issued by the European Patent Office in corresponding European Application No. 11800486.0.
Communication dated Sep. 17, 2013, issued by the Japan Patent Office in corresponding Japanese Application No. 2012-522487.
Omichi et al., "Temperature Monitoring of Superconducting Wire for Quench Detection", 21st International Conference on Optical Fiber Sensors, Spie, May 17,2011, vol. 7753, pp. 77534N-1 to 77534N-4.
Willsch et al., "Fiber Optical Temperature and Strain Measurements for Monitoring and Quench detection of Superconducting Coils", Proceedings of SPIE, Apr. 14, 2008, vol. 7004, pp. 70045G-1 to 70045G-4.
Wolfgang Ecke, et al., Fiber-Optic Bragg Grating Sensors for Structural Health Monitoring at Cryogenic Temperatures, Proceedings of SPIE, 2007, pp. 653002-1-653002-10, vol. 6530.
International Search Report, PCT/JP2011/058700, Jul. 5, 2011.
Office Action issued by Chinese Patent Office in Chinese Application No. 201180005090.8 mailed Nov. 19, 2013.
Li Jian-she, "A Method for Precise Measuring of Resistance Characteristic Curve of the High Temperature Superconductor", May 31, 2010, pp. 25-27 and 43.

* cited by examiner

METHOD FOR DETECTING NON-SUPERCONDUCTING TRANSITION OF SUPERCONDUCTING WIRE

This application is a continuation application based on a PCT Patent Application No. PCT/JP2011/058700, filed Apr. 6, 2011, whose priority is claimed on Japanese Patent Application No. 2011-057939, filed Mar. 16, 2011, and Japanese Patent Application No. 2010-146304, filed Jun. 28, 2010. The contents of the PCT Application and the Japanese Applications are incorporated herein by reference.

BACKGROUND OF THE INVENTION

1. Field of the Invention

The present invention relates to a method for detecting a non-superconducting transition of a superconducting wire.

2. Description of Related Art

Superconducting wires are applicable to, for example, magnetic resonance imaging devices, superconductive magnets of magnetic levitation railways, magnetic bearings, electric motors and the like, and superconductive cables, and toward such practical use, research for ensuring the reliability during operation of the superconducting wires are being actively conducted.

Since the critical temperature (the temperature of the upper limit indicating superconductivity) is generally lower than an ordinary temperature, a superconductor that constitutes a superconducting wire is used by being cooled to the critical temperature or less using a cooling medium such as liquid helium or liquid nitrogen, or a refrigerator. However, even if a superconducting wire is cooled to the critical temperature or less from the outside, a non-superconducting transition, that is, the transition from the superconducting state to the non-superconducting state would occur due to a thermal disturbance in a predetermined portion of the superconducting wire in some conditions. In this case, the temperature of the superconducting wire increases due to an occurrence of Joule heat, and it accelerates the non-superconducting transition of the surrounding area, leading to the problem of an expansion of the region in a non-superconducting state (quench phenomenon).

Japanese Patent No. 2577682 discloses a method for detecting minute temperature increase from the voltage of a carbon film that is provided on a superconductor, in order to detect slight temperature increase immediately prior to quenching in which the superconductor transitions to a non-superconducting state due to a thermal disturbance. However, the method disclosed in Japanese Patent No. 2577682 utilizes the property of the electrical resistance value being remarkably large with respect to the temperature of the carbon film, in an extremely low-temperature region of several K (Kelvin) from the temperature of liquid helium (refer to FIG. 7 in Japanese Patent No. 2577682). For that reason, it is difficult to apply the method to a high-temperature superconductor in which the critical temperature is 77 K or more (for example, approximately 100 K).

Japanese Unexamined Patent Application, First Publication No. H08-304271 discloses a method for detecting quench of a superconductor that makes polarized light from a light source enters an optical fiber wound around a superconducting wire, detects a phase difference of the polarized light from the optical fiber, and detects an unusual polarization state of the light that has transmitted through the optical fiber.

Also, Japanese Unexamined Patent Application, First Publication No. H07-170721 (particularly in the fourth invention thereof) discloses a method for detecting quench of a superconducting wire in which an optical fiber is attached to the outside of a superconducting wire, and an abnormality of the superconducting wire is detected by measuring the reflected light from the deformation portion of the optical fiber due to mechanical deformation of an unusual portion in the superconducting wire during electrification or by measuring the transmitted light from the other end of the optical fiber.

However, the methods disclosed in Japanese Unexamined Patent Application, First Publication No. H08-304271 and Japanese Unexamined Patent Application, First Publication No. H07-170721 can only determine the presence of an abnormality in an optical fiber by an increase in positional shifting or deformation of an optical fiber due to moving the superconducting wire caused by the quenching. And by the methods, it is not possible to measure the temperature variation in detail.

U.S. Pat. No. 6,072,922 and Wolfgang Ecke et al., "Fiber optical grating sensors for structural health monitoring at cryogenic temperatures", Proceedings of SPIE, Vol. 6530, 653002 (2007) disclose a method for measuring temperature under an extremely low temperature with an optical fiber temperature sensor that uses a fiber Bragg grating (FBG). A FBG is an optical fiber device in which a periodical refractive index modulation (grating) is formed in the core of an optical fiber, and it has a selective reflection property of a specified wavelength (Bragg wavelength) that is determined by the refractive index of the core and the grating period.

In U.S. Pat. No. 6,072,922, a coating material (a coating) such as aluminum (Al) or polymethyl methacrylate (PMMA) with a larger thermal expansion coefficient (TEC) than silica, which is the main component of an optical fiber, is provided around the FBG portion of an optical fiber, to enhance the sensitivity of the temperature sensor by increasing the Bragg wavelength shift due to temperature. Also, a measurement example of strain, temperature, and linear expansion is shown in Non-patent Document 1.

U.S. Pat. No. 6,072,922 and Wolfgang Ecke et al., "Fiber optical grating sensors for structural health monitoring at cryogenic temperatures", Proceedings of SPIE, Vol. 6530, 653002 (2007) only disclose being able to measure the temperature of a medium in the case of using a FBG provided with a coating material, for example, a FBG provided with a coating material being immersed in a uniform medium as shown in FIG. 21 of U.S. Pat. No. 6,072,922.

Also, in the case of using the FBG disclosed in U.S. Pat. No. 6,072,922 for temperature measurement of a high-temperature superconductor, since a high-temperature superconductor in the shape of a wire is lacking in a deformation property, it is not possible to place the superconducting wire completely around the wire. That is to say, the medium around an FBG provided with a coating material cannot be made homogeneous. Also, in consideration of the thermal conductivity from the wire, even if the coating material around an optical fiber is firmly attached to a superconducting wire, since difference of the thermal expansion coefficient between the coating material and the superconducting wire, the expansion/contraction of the coating material is restricted. For this reason, there is a risk of having an adverse influence on accuracy and response speed of temperature measurement.

The present invention has been achieved in view of the above circumstances, and has an object to provide a method for detecting the non-superconducting transition of a superconducting wire that, in addition to detecting the temperature variation accompanying the non-superconducting transition with high accuracy and responsiveness, can detect with greater precision the state of a superconducting wire in which the non-superconducting transition has occurred based on a temperature variation of the superconducting wire.

SUMMARY OF THE INVENTION

In order to solve the aforementioned problems, the present invention includes the following structure.

A method for detecting a non-superconducting transition of a superconducting wire according to a first aspect of the present invention is a method for detecting the non-superconducting transition of a superconducting wire including a substrate, a superconducting layer that has a critical temperature of 77 K or more, and a metal stabilization layer, the method including: adhesively attaching an optical fiber in which a plurality of fiber Bragg gratings are formed in a core along a longitudinal direction thereof to the superconducting wire; measuring in advance a Bragg wavelength shift of the fiber Bragg gratings with respect to a temperature variation of the superconducting wire, and determining a relational expression based on the Bragg wavelength shift for a temperature calculation of the superconducting wire; determining temperature variations of the plurality of fiber Bragg gratings before and after non-superconducting transition of the superconducting wire using the relational expression; and calculating a propagation rate of the non-superconducting transition based on both a time difference of temperature increases of the plurality of fiber Bragg gratings, and an interval between each of the fiber Bragg gratings.

In the method for detecting a non-superconducting transition of a superconducting wire according to the aforementioned first aspect of the present invention, a maximum temperature at a starting point of the non-superconducting transition that equals to $(L/V)\upsilon+Tmax$ may be calculated, wherein Tmax is a maximum temperature measured at any of the plurality of fiber Bragg gratings, L is a distance between the fiber Bragg grating and the starting point of the non-superconducting transition, $\upsilon$ is a temperature increasing rate of the fiber Bragg grating, and V is a propagation rate of the non-superconducting transition.

In the method for detecting a non-superconducting transition of a superconducting wire according to the aforementioned first aspect of the present invention, the maximum temperature Tmax and the temperature increasing rate $\upsilon$ may be measured using the fiber Bragg grating closest to the starting point of the non-superconducting transition.

In the method for detecting a non-superconducting transition of a superconducting wire according to the aforementioned first aspect of the present invention, the temperature increasing rate of the respective fiber Bragg gratings may be determined based on the temperature variation of the respective fiber Bragg gratings, and propagation of the non-superconducting transition to a position of the fiber Bragg grating may be determined when the temperature increasing rate is equal to or greater than a predetermined threshold value.

In the method for detecting a non-superconducting transition of a superconducting wire according to the aforementioned first aspect of the present invention, the predetermined threshold value may be set in advance based on a value of an injected current of the superconducting wire.

A method for detecting a non-superconducting transition of a superconducting wire according to a second aspect of the present invention is a method for detecting the non-superconducting transition of a superconducting wire including a substrate, a superconducting layer that has a critical temperature of 77 K or more, and a metal stabilization layer, the method including: adhesively attaching an optical fiber in which a plurality of fiber Bragg gratings are formed in a core along a longitudinal direction thereof to the superconducting wire; measuring in advance a Bragg wavelength shift of the fiber Bragg gratings with respect to a temperature variation of the superconducting wire, and determining a relational expression based on the Bragg wavelength shift for a temperature calculation of the superconducting wire; determining temperature variations of the plurality of fiber Bragg gratings before and after the non-superconducting transition using the relational expression; determining the temperature increasing rate of the respective fiber Bragg gratings based on the temperature variation of the respective fiber Bragg gratings; and determining whether or not the non-superconducting transition is propagated to a position portion of the fiber Bragg grating based on whether or not the temperature increasing rate is equal to or greater than a predetermined threshold value.

In the method for detecting a non-superconducting transition of a superconducting wire according to the aforementioned second aspect of the present invention, a range of the non-superconducting transition may be estimated by doubling a distance between a starting point of the non-superconducting transition and a farthest fiber Bragg grating from the starting point among the fiber Bragg gratings which are determined that the non-superconducting transition is propagated to the fiber Bragg gratings.

In the method for detecting a non-superconducting transition of a superconducting wire according to the aforementioned second aspect of the present invention, the predetermined threshold value may be set in advance based on a value of an injected current of the superconducting wire.

In the method for detecting a value of an injected current transition of a superconducting wire according to the aforementioned second aspect of the present invention, the method including: a Bragg wavelength shift of the fiber Bragg gratings due to electromagnetic force generated by the superconducting wire, the superconducting wire being formed in a coiled manner, may be measured in advance; and the temperature variation of the plurality of fiber Bragg gratings before and after the non-superconducting transition of the superconducting wire may be determined, using a Bragg wavelength shift in the relational expression, the Bragg wavelength shift being obtained by subtracting the Bragg wavelength shift of the fiber Bragg gratings due to the electromagnetic force.

The optical fiber in which a plurality of fiber Bragg gratings are formed may be connected to a temperature measurement instrument including, a broadband light source, a spectroscopic element, an optical device where measurement light from the broadband light source enters and that makes a Bragg reflection light from the plurality of fiber Bragg gratings enter the spectroscopic element, and a light receiving element that detects a light dispersed by the spectroscopic element and outputs a voltage signal.

According to the method for detecting the non-superconducting transition of a superconducting wire according to the aspects of the present invention, by measuring in advance the Bragg wavelength shift of an FBG with respect to a temperature variation of the superconducting wire, and measuring the temperature variation of the superconducting wire using a relational expression for measuring the temperature of the superconducting wire from the Bragg wavelength shift, it is possible to detect the temperature variation accompanying the non-superconducting transition with high responsiveness.

By forming a plurality of FBGs along the longitudinal direction of the optical fiber and measuring the time difference in the start of the temperature increase among these FBGs, it is possible to calculate the propagation rate of the non-superconducting transition from this time difference and the interval of the plurality of FBGs.

By measuring the maximum temperature measured in any FBG, the distance from the FBG to the starting point of the non-superconducting transition, the temperature increasing rate in the FBG, and the propagation rate of the non-superconducting transition, it is possible to determine the maximum temperature in the starting point of the non-superconducting transition.

When the non-superconducting transition propagates to the position of the FBG, by utilizing the fact that the temperature increasing rate is higher compared to that not being the case, it is possible to also determine whether or not the non-superconducting transition has propagated from the temperature increasing rate of the FBG.

Among the plurality of FBGs to which the non-superconducting transition is determined to have propagated, it is also possible to estimate the range in which the non-superconducting transition has occurred based on the distance from the starting point of the non-superconducting transition to the farthest FBG With the superconducting wire being in a coiled manner, and in the case of electromagnetic force being generated in this coil, by using the result of subtracted Bragg wavelength shift of the FBG due to the electromagnetic force, it is possible to more accurately determine the temperature variation produced in the superconducting wire without converting the Bragg wavelength shift due to the electromagnetic force into a temperature variation.

DETAILED DESCRIPTION OF THE INVENTION

Hereinbelow, one exemplary embodiment of the present invention is described with reference to the drawings.

Figure 3:
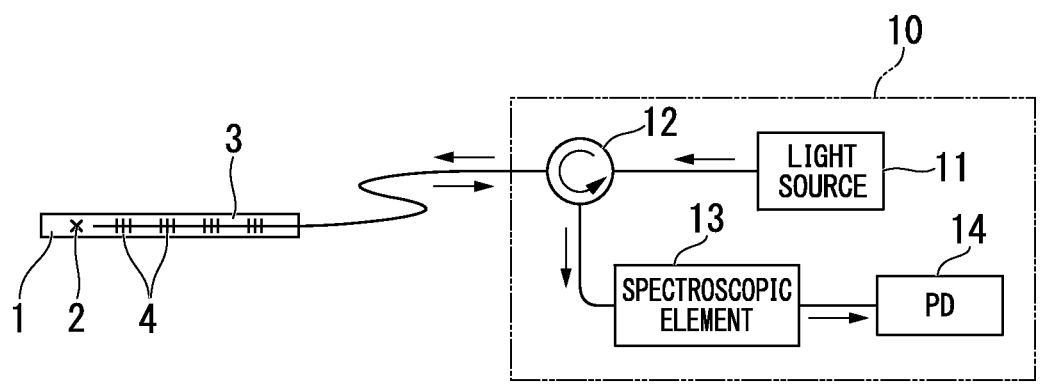
FIG. 3 is a configuration drawing that shows one example of a temperature measuring instrument that uses a plurality of FBGs.
Figure 4:
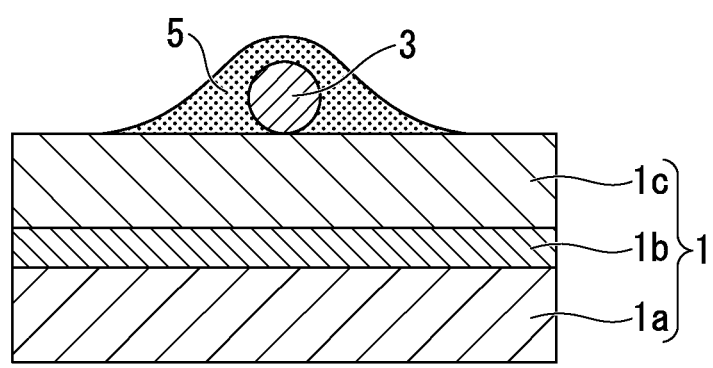
FIG. 4 is a cross-sectional drawing that shows an example of the state of an optical fiber being adhesively attached to the metal stabilization layer of a superconducting wire.

FIG. 3 shows one example of a temperature measuring instrument 10 using an optical fiber 3 in which a plurality of fiber Bragg gratings 4 are formed. Also, FIG. 4 shows one example of the state of the optical fiber 3 being adhesively attached to a metal stabilization layer 1c of a superconducting wire 1.

Superconducting Wire

The superconducting wire 1 is constituted by being provided with at least a substrate 1a, a superconducting layer 1b that has a critical temperature of 77 K or more, and a metal stabilization layer 1c.

As the substrate 1a applicable to the superconducting wire 1 of the present exemplary embodiment, a substrate for an ordinary superconducting wire can be used, and may have high strength. Moreover, the substrate preferably has a tape-shape in order to serve as a long cable, and preferably includes a metal that has heat resistance required for the film formation process of the superconductor and the like. Examples of the metal substrate include various metallic materials such as silver, platinum, stainless steel, copper, and nickel alloys such as Hastelloy (registered trademark), or various metallic materials having ceramic materials provided thereon. Among the various heat-resistant metals, nickel alloy is preferred. Among these, in the case of a commercialized product, Hastelloy (trade name registered to Hanes International of the U.S.) is preferred. As Hastelloy, it is possible to use any of the types of Hastelloy B, C, G, N, W or the like, in which the amounts of molybdenum, chromium, iron, cobalt and the like differ from each other. The thickness of the substrate 1a may be suitably adjusted in accordance with the object, and ordinarily is 10 to 500 μm.

The superconductor that constitutes the superconducting layer 1b may be a publicly known superconductor as long as it has a critical temperature of 77 K or more, and specific examples include a superconductor with a composition expressed by $REBa_2Cu_3O_y$, (where RE denotes a rare earth such as Y, La, Nd, Sm, Er, Gd and the like). Examples of this superconducting layer include Y123 ($YBa_2Cu_3O_{7-x}$) or Gd123 ($GdBa_2Cu_3O_{7-x}$). Also, a superconductor that includes another oxide superconductor, for example another oxide superconductor with a high critical temperature represented by the composition $Bi_2Sr_2Ca_{n-1}Cu_nO_{4+2n+\delta}$ may be used.

Although the thickness of the superconducting layer 1b is not particularly limited, it is preferably about 0.5 to 5 μm, with a uniform thickness.

The superconducting layer 1b can be deposited by sputtering, vacuum evaporation, laser evaporation, electron beam evaporation, pulsed laser deposition (PLD), ion beam assisted deposition (IBAD), chemical vapor deposition (CVD) and the like, with PLD and IBAD among these being preferred from the aspect of productivity.

Also, metallo-organic decomposition (MOD) is suitable for manufacturing a long, tape-shaped superconductor because it does not require a vacuum process and enables low-cost and high-speed film formation. It includes a coating process that uniformly dissolved metal-organic compounds are coated onto a substrate, and a thin film formation process that the coated compounds are thermally decomposed onto the substrate.

The metal stabilization layer 1c that is deposited on the superconducting layer 1b includes a metallic material with preferable conductivity, and it acts as a bypass through which the current of the superconducting layer 1b is commuted when the superconducting layer 1b transits from a superconducting state to a non-superconducting state. The metallic material that constitutes the metal stabilization layer 1c may be a material that has good electrical conductivity, and although not particularly limited, is preferably one that is comparatively low priced such as an alloy like copper or brass (Cu—Zn alloy), or stainless steel or the like, and more preferably copper since it has high electrical conductivity among these and is inexpensive. Thereby, it becomes possible to achieve a thick film of the metal stabilization layer 1c while keeping down material costs, and the superconducting wire 1 that can withstand a fault current can be obtained at a low price. The thickness of the metal stabilization layer 1c is preferably 10 to 300 μm. The metal stabilization layer 1c can be formed by a publicly known method, for example, it can be formed by sputtering and a method for soldering metal tape such as copper.

One or two or more optional layers chosen from a diffusion prevention layer, a bed layer, an intermediate layer, a cap layer and the like may be interposed between the substrate 1a and the superconducting layer 1b.

The diffusion prevention layer is formed to prevent the diffusion of the constituent elements of the substrate, and is constituted from silicon nitride ($Si_3N_4$), aluminum oxide ($Al_2O_3$), or a rare earth metal oxide and the like. The diffusion prevention layer is formed, for example, by a film formation method such as sputtering, and its thickness is for example 10 to 400 nm.

The bed layer is formed to obtain the orientation of the film to be arranged thereon, and for example is constituted from for example yttrium oxide ($Y_2O_3$), silicon nitride ($Si_3N_4$), aluminum oxide ($Al_2O_3$) and the like. The bed layer is formed by a film formation method such as sputtering, and its thickness is for example 10 to 200 nm.

The intermediate layer is constituted from a material with a biaxial orientation in order to control the crystal orientation of the superconducting layer. The intermediate layer may be either of a single layer structure or a multi-layer structure, and preferred materials include metal oxides such as $Gd_2Zr_2O_7$, MgO, $ZrO_2$—$Y_2O_3$ (YSZ), $SrTiO_3$, $CeO_2$, $Y_2O_3$, $Al_2O_3$, $Gd_2O_3$, $Zr_2O_3$, $Ho_2O_3$, $Nd_2O_3$ and the like. The intermediate layer can be deposited by a publicly known method such as a physical evaporation method like sputtering, vacuum evaporation, laser evaporation, electron-beam evaporation, ion beam assisted deposition (IBAD), and chemical vapor deposition (CVD), and metallo-organic decomposition (MOD). The thickness of the intermediate layer can be suitably adjusted, however, it is preferably in a range of 0.005 to 2 μm.

The cap layer is preferably formed by a process that crystal grains selectively grow in the planar direction by being epitaxially grown on the surface of the intermediate layer, and subsequently overgrown in the lateral direction (a direction parallel with the surface). With such the cap layer, since a higher in-plane orientation is obtained than the intermediate layer that is made of a metal oxide layer, it is preferable to form the superconducting layer on the cap layer. Provided the material of the cap layer can exhibit the aforementioned functions, it is not particularly limited, however, detailed examples of preferred materials include $CeO_2$, $Y_2O_3$, $Al_2O_3$, $Gd_2O_3$, $Zr_2O_3$, $Ho_2O_3$, $Nd_2O_3$ and the like. Also, the cap layer may include a Ce-M—O oxide in which a portion of Ce in $CeO_2$ is substituted with another metal atom or metal ion.

It is possible to form a layer as a metal stabilization base layer between the superconducting layer 1b and the metal stabilization layer 1c. It includes a metallic material with good electrical conductivity such as Ag, and it has low contact resistance (interfacial electrical resistance) with the superconducting layer 1b. It is possible to form the metal stabilization base layer by a publicly known method such as sputtering, and the thickness is preferably 1 to 30 μm.

Optical Fiber

With respect to the superconducting wire 1 of the present exemplary embodiment, an optical fiber 3 is adhesively attached to the metal stabilization layer 1c. The optical fiber 3 may be a publicly known optical fiber that allows formation of a fiber Bragg grating (FBG), and preferably, a silica-based single-mode optical fiber. The material that constitutes the silica-based optical fiber can be suitably selected from a pure silica glass, a silica glass that uses dopants to raise the refractive index such as germanium (Ge) or the like, or a silica glass that uses dopants to lower the refractive index such as fluorine (F) or the like. Also, it is possible to provide a coating material around the cladding in a concentric manner in cross section. Specific examples of the coating material include resins with a high Young's modulus such as polyimide, and metals such as copper (Cu) and nickel (Ni), and it is possible to make a selection in consideration of the adhesiveness with an adhesive layer 5 described below.

The optical fiber 3 may be adhesively attached in contact with or approaching the metal stabilization layer 1c of the superconducting layer 1. The material of the adhesive layer 5 is preferably a material with a high durability in low temperatures and a high Young's modulus so as to protect the optical fiber 3 even at low temperatures. Examples of the adhesive layer 5 include resins such as polyimide and bond metals.

Methods of forming an FBG in the optical fiber 3 include, in the case of the core being Ge doped silica glass, inducing a predetermined periodical refractive index modulation along the longitudinal direction of the core by a phase mask exposure method or a two-beam interference exposure method using, for example, a krypton fluoride (KrF) excimer laser, an argon (Ar) SHG (second harmonic generation) laser.

The period (spacing) of the grating (diffraction grating) can be set up in consideration of the refractive index of an optical fiber and the like so that the Bragg reflection may arise within the wavelength band of the measurement light. For example, as for the period of a grating, when using 1.5-μm band measurement light for a silica glass optical fiber, the period of the grating is preferably about 0.5 μm.

The length in one grating (grating length) can be suitably selected in accordance with the desired reflectivity and reflection bandwidth, and is preferably for example 1 to 10 mm.

Note that with the interval of the diffraction grating being $\Lambda$, the wavelength of light in a vacuum being $\lambda$, the refractive index of the optical fiber core being n, and incident angle being $\theta$, and an arbitrary positive integer being N, since the condition of Bragg reflection is $2\Lambda \sin\theta = N\lambda/n$, if $\theta$ is assumed to be a right angle ($\sin\theta=1$), and the integer N is 1, between the lattice interval $\Lambda$ and the Bragg wavelength $\lambda_B$, there is the relationship of $\lambda_B = 2\,n\Lambda$.

When a temperature variation occurs in this FBG the Bragg wavelength $\lambda_B$ changes due to the change of both the refractive index n and the lattice interval $\Lambda$. The change of the refractive index n depends on the material of the optical fiber core, and hardly depends on the coating material of the optical fiber 3 and the object to be adhesively attached. On the other hand, since a change of the lattice interval $\Lambda$ occurs by deformation (expansion and contraction) along the longitudinal direction of the optical fiber 3, it depends on the coating material of the optical fiber 3 and the object to be adhesively attached.

When the optical fiber 3 with an FBG is adhesively attached to the superconducting wire 1, even if the linear expansion coefficient of the silica glass itself that constitutes the optical fiber 3 is small, since the linear expansion coefficient of the member that constitutes the superconducting wire 1 is large, a large linear expansion is occurred during a temperature increasing. That is to say, during a temperature increasing, the lattice interval $\Lambda$ of the FBG extends due to the linear expansion of the superconducting wire 1, and the Bragg wavelength $\lambda_B$ shifts to a longer wavelength.

Method for Measuring Temperature of Superconducting Wire

In the method for measuring the temperature of the superconducting wire used in the present invention, while adhesively attaching an optical fiber 3, in which a plurality of fiber Bragg gratings are formed in a core, to the metal stabilization layer 1c, a Bragg wavelength shift of the FBGs with respect to a temperature variation of the superconducting wire 1 is measured in advance. Furthermore, a relational expression based on the Bragg wavelength shift for a temperature calculation of the superconducting wire is determined. Thereby, it is possible to measure in real time the temperature of the superconducting wire 1 from the Bragg wavelength shift.

Since this relational expression is a function that expresses the correlation between the Bragg wavelength shift and the temperature of the superconducting wire 1, by determining a function that expresses the temperature dependency of the Bragg wavelength shift in advance (that is to say, the correlation between the temperature and the Bragg wavelength shift) through an actual measurement, it is possible to derive it as the inverse function.

The temperature range necessary to measure the temperature dependency of the Bragg wavelength shift in advance is a predetermined temperature variation in which the temperature measurement of the superconducting wire 1 is required. The temperature range when the superconducting wire 1 is operated in a superconducting state preferably includes the temperature range that can be attained after the non-superconducting transition of the superconducting wire 1 has occurred.

A temperature measuring instrument 10 shown in FIG. 3 is provided with the optical fiber 3 in which a plurality of fiber Bragg gratings 4 are formed, a broadband light source 11, a spectroscopic element 13, an optical device 12 that makes a measurement light from the broadband light source 11 enter the optical fiber 3, and makes a Bragg reflection light from the plurality of fiber Bragg gratings 4 enter the spectroscopic element 13, and a light receiving element 14 that receives the light dispersed by the spectroscopic element 13 and outputs a voltage signal. The incident side of the optical fiber 3 that is close to the light source 11 is connected to the optical device 12 of the temperature measuring instrument 10.

When measuring the temperature dependency of a Bragg wavelength shift, the Bragg wavelength is measured while changing the ambient temperature with a refrigerator or the like, in the state of the optical fiber 3 being adhesively attached to the metal stabilization layer 1c of the superconducting wire 1.

As the light source 11, it is preferable to use a broadband light source that can arbitrarily output the entire range of Bragg wavelengths that each FBG can take in the measurement. In the case of the wavelength range of the measurement light that is required for temperature measurement being wide, it is possible to achieve compatibility by combining a plurality of light sources with different output wavelength ranges, and making light from a suitable light source enter the optical fiber 3.

The optical device 12 that is interposed between the broadband light source 11 and the optical fiber 3 is not particularly limited as long as it has a function that makes the measurement light from the broadband light source 11 enter the optical fiber 3, and makes the Bragg reflection light enter the spectroscopic element 13. A specific example includes a circulator. The optical device 12 may also be a coupler, however, in order to prevent the reflection light from returning to the light source 11, it is preferable to provide an isolator that causes light to be transmitted only in the direction from the light source 11 to the optical device 12.

As shown in FIG. 3, the measurement light from the light source 11 enters the optical fiber 3, and the spectrum of the reflected light is measured. In order to distinguish between the Bragg wavelengths of the plurality of FBGs, the Bragg wavelength values may be made to differ from each other. Since there is a temperature dependency in the Bragg wavelength, it is preferable to provide a wavelength difference for each FBG to prevent wavelength overlap in the temperature measurement. As for the spectrum of reflected light, by receiving the reflected light with the light receiving element 14 via the spectroscopic element 13 that can arbitrarily select the transmitted wavelength within a predetermined wavelength range, it is possible to measure the spectrum of reflected light as the wavelength dependency of optical power.

As an alternative method for the temperature measuring instrument 10 described above, it is also possible to use a configuration that employs a tunable laser for the light source 11, and inputs Bragg reflection light to the light receiving element 14 without using the spectroscopic element 13. In this case, the tunable laser preferably performs wavelength sweeps of the Bragg wavelengths of the plurality of FBGs within the measurable range.

Also, by forming the temperature measuring instrument 10 based on the publicly known time division multiplexing (TDM) or optical frequency domain reflectometry (OFDR), it is possible to use FBGs with a same Bragg wavelength for the temperature measurement of the superconducting wire 1.

As described above, the optical fiber 3 is adhesively attached to the superconducting wire 1, and the Bragg wavelength shifts due to the linear expansion of the superconducting wire 1 accompanying a temperature variation. Generally, the temperature dependency of a linear expansion coefficient of a metallic material that constitutes the substrate or the metal stabilization layer of the superconducting wire is approximated by a polynomial equation (since the sectional area of the superconducting layer is sufficiently small compared with the substrate and the metal stabilization layer, the linear expansion coefficient of the superconducting wire is dominated to the characteristics of these metallic materials). For this reason, when the relational expression showing the temperature dependency of the Bragg wavelength is expressed as a simple linear equation, it is difficult to sufficiently approximate in a wide temperature range from under the critical temperature to around a normal temperature. Therefore, when for example, using a single high-order equation such as a fourth-order expression, it is possible to approximate with a high precision in the wide temperature range, which is preferred. Instead of the single equation, it is possible to express this relational expression with polygonal line functions by dividing the domain into some small ranges, and using linear equations that differ for each of the small range.

Also, the temperature measuring instrument 10 shown in FIG. 3 also can be used for continuously measuring the Bragg wavelength of each FBG of the optical fiber 3 during operation of the superconducting wire 1. Since a relational expression that expresses the correspondence from the Bragg wavelength to the temperature is found in advance, it is possible to convert the Bragg wavelength measured in real time as a temperature of the superconducting wire 1 instantly.

When a current is injected to the superconducting wire 1 at the critical temperature or less, the superconducting layer 1b is in a superconducting state. Since the resistance value is 0, the electrical current flows through the superconducting layer 1b, and heat generation is not induced in the superconducting wire 1.

In the superconducting wire 1, even when for whatever reason, a non-superconducting transition occurs in which the superconducting layer 1b transits from the superconducting state to the non-superconducting state, electrical resistance is occurred in the superconducting layer 1b, and electrical current flows through the metal stabilization layer 1c because it has comparatively little resistance. In that event, Joule heat is generated in the metal stabilization layer 1c in accordance with the current value and resistance value, and heat generation is induced.

The linear expansion of this superconducting wire occurs at an extremely fast time constant with respect to the heat generation. Even when a non-superconducting transition occurs in the superconducting wire 1 of the present exemplary embodiment, since the optical fiber 3 in which a plurality of FBGs are formed being adhesively attached to the metal stabilization layer 1c of the superconducting wire 1, it is possible to detect the temperature variation (temperature increase) in the superconducting wire 1 with high precision and responsiveness. That is to say, according to the method for measuring the temperature of a superconducting wire of the present exemplary embodiment, excellent responsiveness can be obtained. Since the linear expansion of the superconducting wire 1 should be sufficiently transferred, the optical fiber 3 may be adhesively attached to the front surface of the substrate 1a or a side surface of the superconducting wire 1.

Figure 1:
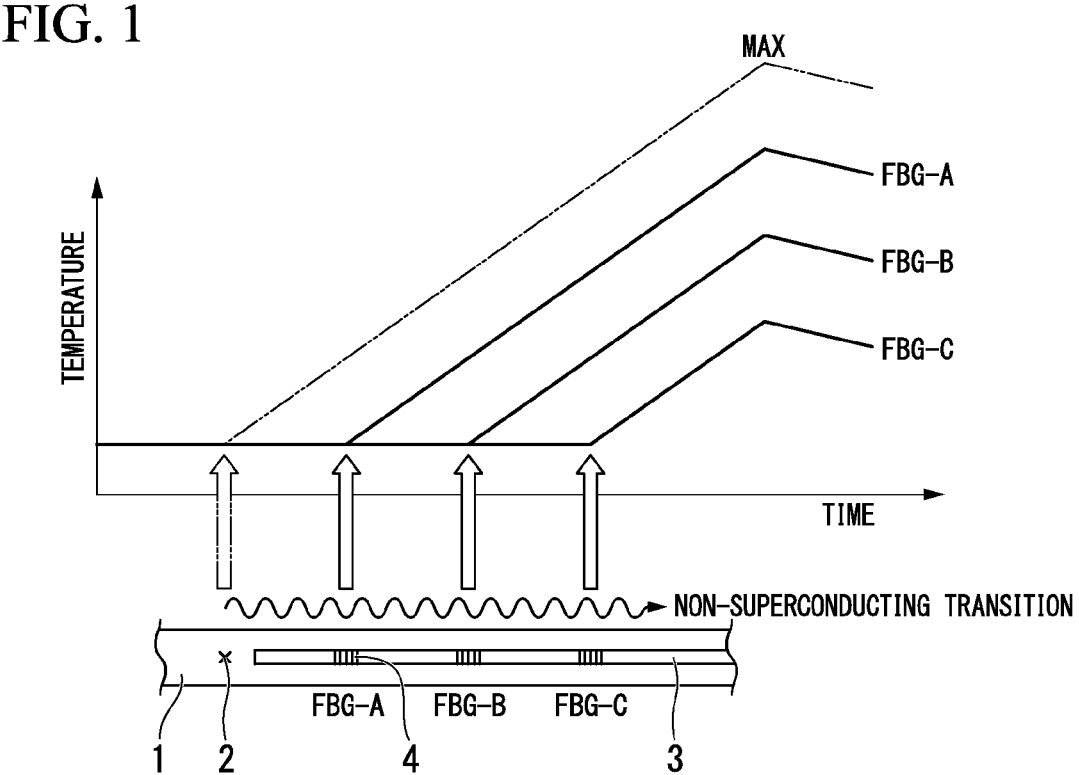
FIG. 1 is a conceptual drawing that describes the method for determining the maximum temperature in the starting point of the non-superconducting transition according to one exemplary embodiment of the present invention.
Figure 2:
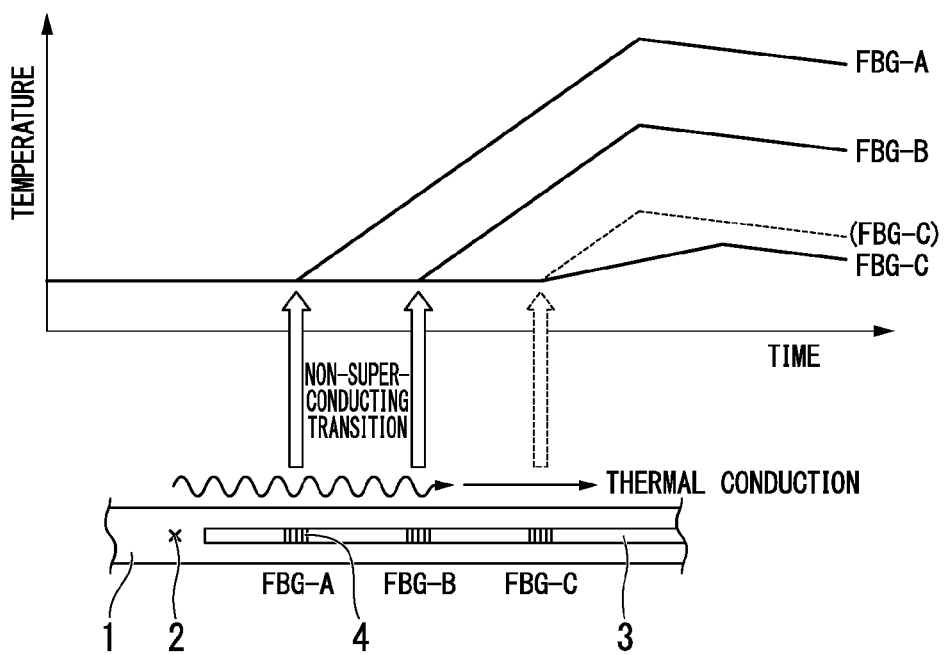
FIG. 2 is a conceptual drawing that describes the method for judging whether or not the non-superconducting transition has propagated to the position of an FBG according to one exemplary embodiment of the present invention.

When the non-superconducting transition of the superconducting wire 1 occurs at one location, since the Joule heat that occurs at the starting point 2 is thermally conducted to the vicinity thereof, further causing a non-superconducting transition, the range of the non-superconducting transition expands on both sides along the longitudinal direction of the superconducting wire 1. In the present exemplary embodiment, since a plurality of FBGs are provided along the longitudinal direction of the optical fiber 3, it is possible to measure the temperature variation (the change in temperature over the time) at a plurality of positions that differ from the starting point 2 of the non-superconducting transition, as shown in FIGS. 1 and 2. Then, by comparing the temperature variation at the plurality of FBGs, it is possible to analyze in detail the generation state and propagation state of the non-superconducting transition.

Propagation Speed of Non-Superconducting Transition

As shown in FIG. 1, when the temperature variation of FBGs is continuously measured from before to after the non-superconducting transition occurs in the superconducting wire 1, it is possible to determine the starting time of the temperature increase of the FBGs. Specifically, if the temperature variation in the time range prior to the occurrence of the non-superconducting transition is considered a baseline, the start of the temperature increase is found from the position on the time axis where the line (or the tangent thereof), which shows the temperature variation (temperature increase) after the non-superconducting transition has occurred, intersects with the baseline.

It is possible to calculate the propagation rate of the non-superconducting transition from the difference in the starting time of the temperature increase of the plurality of FBGs, and the interval of the plurality of FBGs. As the interval of the plurality of FBGs, it is possible to use a value set in advance when forming the core of the optical fiber, and is already known. In the case of the number of FBGs being two, the quotient obtained by dividing the FBG interval by the time difference of the temperature increase is equivalent to the propagation rate of the non-superconducting transition. In the case of the number of FBGs being three or more, it is possible to determine the propagation rate of the non-superconducting transition in the same way by a statistical method such as taking an average.

Estimation of the Highest Temperature

Since the superconducting wire is cooled using a cooling medium or refrigerator, the temperature of the superconducting wire prior to the occurrence of the non-superconducting transition is uniform at all places. Also, since the material and structure of the superconducting wire is approximately uniform over the entirety in the longitudinal direction, the temperature increasing rates at the locations where the non-superconducting transition occurs is approximately equal at all places. Note that the temperature increasing rate is the temperature difference of rising per unit time, and for example can be found by averaging the time differentiation of a temperature variation.

Therefore, the maximum temperature $Tmax_{FBG}$ in the FBG, in which the non-superconducting transition has propagated, can be found by the approximation $Tmax_{FBG} \approx T_0 + \upsilon \Delta t_1$, where $T_0$ is the temperature of the superconducting wire 1 prior to the occurrence of non-superconducting transition, $\upsilon$ is the temperature increasing rate due to the non-superconducting transition, and $\Delta t_1$ is the time difference from after the start of the temperature increase to the attaining of the maximum temperature at the position of the FBG.

Also, the time difference $\Delta t_0$ from after the non-superconducting transition initially occurs at the starting point 2 of the non-superconducting transition to the start of the temperature increase at the FBG that is nearest to the starting point 2 can be found by $\Delta t_0 = L/V$, with the distance L from the starting point 2 of the non-superconducting transition to this FBG, assuming the propagation rate V of the non-superconducting transition is constant.

Moreover, the completion of the temperature increase occurs almost simultaneously across the entire superconducting wire, due to common reasons, such as restriction and shutoff of electricity to the superconducting wire 1, and the like. That is to say, the time difference from after the initial occurrence of the non-superconducting transition to the completion of the temperature increase is $\Delta t_0 + \Delta t_1$.

In the case of modeling the temperature increase process of a superconducting wire in which a non-superconducting transition has occurred in this way, at the starting point 2 of the non-superconducting transition, since the temperature increase continues from time from after the initial occurrence of the non-superconducting transition to the completion of the temperature ($\Delta t_0 + \Delta t_1$) at the temperature increasing rate $\upsilon$, it is possible to determine the maximum temperature $Tmax_O$ at the starting point 2 of the non-superconducting transition by the approximation $Tmax_O \approx T_0 + \upsilon \times (\Delta t_0 + \Delta t_1) = (T_0 + \upsilon \Delta t_1) + \upsilon \Delta t_0 \approx Tmax_{FBG} + \upsilon \times (L/V)$.

That is to say, in any of the plurality of FBGs, letting the maximum temperature be Tmax (corresponding to the aforementioned $Tmax_{FBG}$), the distance from this FBG to the starting point 2 of the non-superconducting transition be L, and the temperature increasing rate in this FBG be $\upsilon$, the maximum temperature $Tmax_0$ that equals to $(L/V)\upsilon + Tmax$ at the starting point 2 of the non-superconducting transition can be calculated.

Note that since some difference may occur in the value of the temperature increasing rate $\upsilon$ in the FBG in accordance with the distance from the starting point 2, in order to determine the maximum temperature at the starting point 2 of the non-superconducting transition with greater accuracy, it is preferable to use a temperature variation that is measured by the FBG that is closest to the starting point 2.

Propagation Range of Non-Superconducting Transition

As shown in FIG. 2, in the case of the non-superconducting transition not reaching a distant FBG due to the temperature increase being completed in a comparatively short time, the heat generation due to the thermal conduction from the side close to the starting point 2 at that FBG (FBG-C in FIG. 2) may be measured. However, since the heat generation due to the thermal conduction is small compared to the heat generation due to the non-superconducting transition at the FBG position, it is possible to distinguish both by a comparison of the temperature increasing rate.

Therefore, by determining the temperature increasing rate at each of the plurality of FBGs from the temperature variation of each FBG; and determining whether the temperature increasing rate is equal to or greater than a predetermined threshold value, it is possible to determine whether or not the non-superconducting transition has propagated to the position of that FBG Note that in the case of estimating the propagation rate of the non-superconducting transition and the maximum temperature as described above, it is necessary for the non-superconducting transition to propagate until the position of the FBG used for the estimation. If the temperature increasing rate of that FBG is equal to or greater than the predetermined threshold value, it is possible to confirm that the non-superconducting transition has propagated to the position of that FBG Also, among the FBGs to which the non-superconducting transition is determined to have propagated, by doubling the distance from the starting point 2 of the non-superconducting transition to the farthest FBG, it is possible to estimate the range in which the non-superconducting transition occurs. In the example shown in FIG. 2, since the FBG that is farthest from the starting point 2 of the non-superconducting transition is FBG-B, the propagation range of the non-superconducting transition can be estimated as double the distance from the starting point 2 to the FBG-B.

As described above, the heat generation due to the non-superconducting transition is mainly Joule heat corresponding to the current value that flows in the metal stabilization layer 1c and the resistance value of the metal stabilization layer 1c. Since the amount of heat generation strongly depends on the current value, with regard to the aforementioned predetermined threshold value for judging whether or not the non-superconducting transition has propagated to the position of the FBG, it is preferable to set the value that differs based on an injected current value of the superconducting wire.

Note that with regard to the heat generation due to the thermal conduction, since the restriction and shutoff of electricity to the superconducting wire 1 does not directly stop the temperature increase, the time, at which a region heated by thermal conduction shows the maximum temperature, is not always constant at all locations. From this aspect as well, it is possible to distinguish between the propagation range of the non-superconducting transition and the range where only thermal conduction occurs.

Superconducting Protection Device

The method for detecting the non-superconducting transition of a superconducting wire of the present exemplary embodiment can be used for a protection device of a superconducting wire in operation.

The superconducting wire protection device can be provided with an analyzing device such as a computer that receives an electrical signal outputted from the light receiving element 14 in the temperature measuring instrument 10 of FIG. 3, and automatically analyzes it according to the aforementioned temperature measuring method or method for detecting the non-superconducting transition, a regulator that regulates the amount of injection current to the superconducting wire by limiting (lowering) or shutting off (stopping) the current in the case of an abnormality being detected, an alarm device that gives an alarm to the operator in the case of an abnormality being detected, a display device of the operation state, and a recording device for the temperature history. Thereby, it is possible to prevent fusing and burning loss of the superconducting wire 1 even when a non-superconducting transition occurs, and protect the superconducting wire 1 in a preferable condition.

In particular, since it is possible to quantitatively recognize damage to the superconducting wire due to the non-superconducting transition by measuring the maximum temperature at the starting point of the non-superconducting transition and the range in which the non-superconducting transition occurs, after confirming the safeness, it is possible to restart operation without replacing the superconducting wire if the damage is minor.

Also, in the case of inspection or replacement of the superconducting wire being required, since it is possible to carry out the work after acquiring preliminary information about the extent of the damage, faster and more precise work becomes possible.

Superconducting Coil

The present exemplary embodiment, by making a superconducting wire into a coil shape, can also be applied to a superconducting coil that can generate electromagnetic force (hoop stress) by applying electrical current to the superconducting wire.

The superconducting coil may be a pancake-shaped coil in which a superconducting wire is curved in the thickness direction, and concentrically wound numerous times. Furthermore, two, or three or more coil can be stacked.

In this case, when converting a Bragg wavelength shift to the temperature of a superconducting wire using the relational expression for measuring the temperature of a superconducting wire from the Bragg wavelength shift (change of the Bragg wavelength), as the Bragg wavelength shift to be input (substituted) into this relational expression, it is preferable to apply to the relational expression the Bragg wavelength shift of the result of subtracting the Bragg wavelength shift of the FBG due to the electromagnetic force, and not apply to the relational expression the Bragg wavelength shift that includes as is the Bragg wavelength shift of the FBG due to the electromagnetic force. Thereby, it is possible to more accurately determine the temperature variation that arises in the superconducting wire, without converting the Bragg wavelength shift due to electromagnetic force into a temperature variation.

The Bragg wavelength shift of the FBG due to the electromagnetic force depends on the electrical current value that is applied to the superconducting wire. For this reason, it is preferable to measure the electrical current value that is applied to the superconducting wire and the Bragg wavelength shift due to the electromagnetic force with respect to this current value under the condition of no temperature variation in advance, and determine the relation between the current value and the Bragg wavelength shift due to the electromagnetic force. It is possible to estimate with high accuracy the value of the Bragg wavelength shift due to electromagnetic force from this relation and the current value that is actually applied.

Hereinabove, the present invention has been described based on a preferred exemplary embodiment, however, the present invention is not limited the aforementioned exemplary embodiment, and various modifications can be made within a scope that does not depart from the gist of the present invention.

EXAMPLES

Hereinbelow, the present invention is explained in more detail with Examples, however, the present invention is not limited to the following Examples.

Example 1 of Method for Measuring Temperature

In the temperature measuring instrument 10 of the superconducting wire 1 shown in FIG. 3, the optical fiber 3 is adhesively attached to the superconducting wire 1 as shown in FIG. 4.

In the present example, Hastelloy C276 with a width of 5 mm and a thickness of 0.1 mm is used for the substrate 1a of the superconducting wire 1. GdBCO ($GdBa_2Cu_3O_{7-x}$) with a width of 5 mm and a thickness of 0.001 mm (that is 1 μm) is used for the superconducting layer 1b. The critical temperature of this superconducting layer is approximately 90 K, and the critical current is approximately 230 A (the value under an environment of a temperature of 77 K and a magnetic field of 0 T). Copper with a width of 5 mm and a thickness of 0.1 mm is used for the metal stabilization layer 1c.

In the optical fiber 3 in which the fiber Bragg gratings 4 (FBG) are formed, the outer diameter of the core that includes Ge doped silica glass is approximately 8 μm, the outer diameter of the cladding that includes pure silica glass is approximately 125 μm, and the periphery of the cladding is coated with a coating layer consisting of polyimide with an outer diameter of 150 μm.

As shown in FIG. 4, the optical fiber 3 in which FBGs are formed is attached to the metal stabilization layer 1c using a polyimide resin (part number PI2525 by HD Micro Systems) as the adhesive layer 5. More specifically, first, the optical fiber 3 is temporarily attached so as to make close contact to the metal stabilization layer 1c. Then, it is attached by applying a polyimide resin that serves as the adhesive layer 5 so as to cover the periphery of the optical fiber 3. And the polyimide resin is cured by heating this coated portion for 1 minute at 200° C.

A series of FBGs 1 to 4 is formed at an interval of 10 mm in the longitudinal direction of the optical fiber 3 that is adhesively attached to the superconducting wire 1. These FBGs are manufactured by a publically known exposure method that uses a KrF excimer laser and a uniform phase mask. In the present exemplary embodiment, the grating length of the FBGs 1 to 4 is 6 mm. Also, they are manufactured with approximately 10 nm wavelength spacing. The target values at room temperature (295 K) without strain are approximately 1540 nm for FBG 1, approximately 1550 nm for FBG 2, approximately 1560 nm for FBG 3, and approximately 1570 for FBG 4. Note that the actual measurement values of the Bragg wavelength will be described later together with the measurement method.

Subsequently, a configuration of the measuring instrument for measuring the Bragg wavelength of the FBGs 1 to 4 shown in FIG. 3 is explained. The measuring instrument is schematically constituted from a broadband light source 11 that launches measurement light, a circulator 12, wavelength reference FBGs 1 and 2 (not illustrated), a spectroscopic element 13 that disperses the Bragg reflection lights of the wavelength reference FBGs 1 and 2 and the FBGs 1 to 4, and a photodiode (PD) 14. In greater detail, an amplified spontaneous emission (ASE) light source is used for the broadband light source 11, and a wavelength tunable filter that utilizes an acousto-optic effect (AOTF) is used for the spectroscopic element 13.

As the ASE light source 11, a light source that launches light in a wavelength range from 1520 to 1610 nm is used, and the total optical output is 50 mW (that is, 17 dBm). The measurement light that is launched from the ASE light source 11 transmits through the circulator 12 to be input into the wavelength reference FBGs 1 and 2 and the FBGs 1 to 4 of the optical fiber 3 that is adhesively attached to the superconducting wire 1. Regarding the measurement light that is input into the FBGs, only selected lights corresponding to the Bragg wavelength of the FBGs are reflected, and they are input into the spectroscopic element 13 via the circulator 12.

The AOTF that is used as the spectroscopic element 13 is constituted from a LiNbO$_3$ based planar lightwave circuit, and by applying a sinusoidal wave with a frequency of 160 to 180 MHz to the comb-shape electrodes provided on the upper surface of the planer lightwave circuit, it is possible to selectively transmitted light in a wavelength range from 1510 to 1680 nm. Since a unique relation between the frequency of the applied sinusoidal wave and the transmitted wavelength, by performing a wavelength sweep digitally (in a stepwise manner) in the aforementioned range with respect to time, it is possible to change the wavelength of the light that is input to the PD 14 with respect to time in the range from 1510 to 1680 nm. In the present exemplary embodiment, the frequency is continuously swept in a range from 160 to 180 MHz in the direction from a high frequency (180 MHz) to a low frequency (160 MHz), assuming the step frequency of the frequency sweep (the frequency interval when performing a stepwise frequency sweep) is 1.5 kHz, and the step time (retention time per one step) is 4 μs. Under these conditions, the time taken for one frequency sweep is approximately 53.3 ms according to Equation (1).

[Equation 1]

$$4 \text{ (μs)} \times \frac{180 - 160 \text{ (MHz)}}{1.5 \text{ (kHz)}} = 53.3 \text{ (ms)} \quad (1)$$

Since it is possible to continuously perform this frequency sweep, measurement of the Bragg wavelength of the FBG is possible at a repetition frequency of 1/0.0533 s, that is to say, 18.75 Hz.

The wavelength reference FBGs 1 and 2 are used for determining the relationship between the frequency of the sinusoidal wave that is applied to the AOTF and the wavelength of the transmitted light. The wavelength reference FBGs 1 and 2 are installed under the environment of the temperature variation being ±1° C. or less, and the strain being ±10με or less (note that 1με=10$^{-4}$%).

The Bragg wavelengths of these wavelength reference FBGs are measured in advance as 1532.100 nm and 1584.500 nm, respectively, at room temperature (295 K) without strain.

Figure 5:
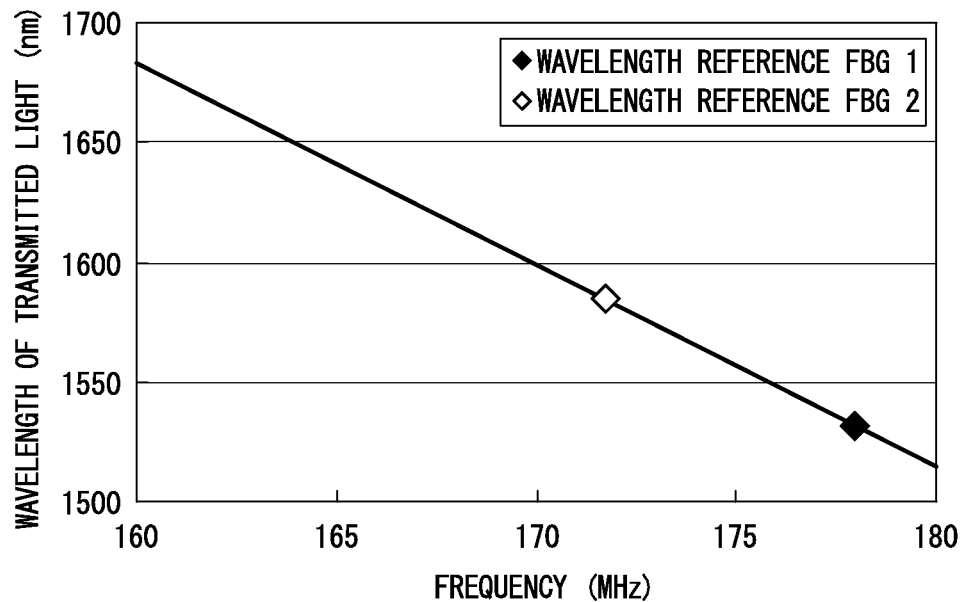
FIG. 5 is a graph that shows one example of the relation between the applied frequency of the spectroscopic element (AOTF) used in the exemplary embodiment and wavelength of the transmitted light.

As a result of measuring the applied frequency when the reflected lights of the wavelength reference FBGs 1 and 2 are transmitted, the applied frequency is 177.95 MHz with respect to the wavelength of the transmitted light being 1532.100 nm, and the applied frequency is 171.70 MHz with respect to the wavelength of the transmitted light being 1584.500 nm. FIG. 5 is a graph that shows the applied frequency of AOTF on the horizontal axis, and the wavelength of the transmitted light on the vertical axis. In this way, by complementing the relation between the applied frequency and the wavelength of the transmitted light with a linear function, it is possible to make the applied frequency and the wavelength of the transmitted light precisely correspond in a 1-to-1 manner.

Note that, since the relation between the applied frequency and the wavelength of the transmitted light is changed depending on changes and fluctuations of the temperature environment and the like, in an actual measurement, the relation is calculated for each one sweep, and the Bragg wavelengths of the FBGs 1 to 4 are determined based on this relation.

Figure 6:
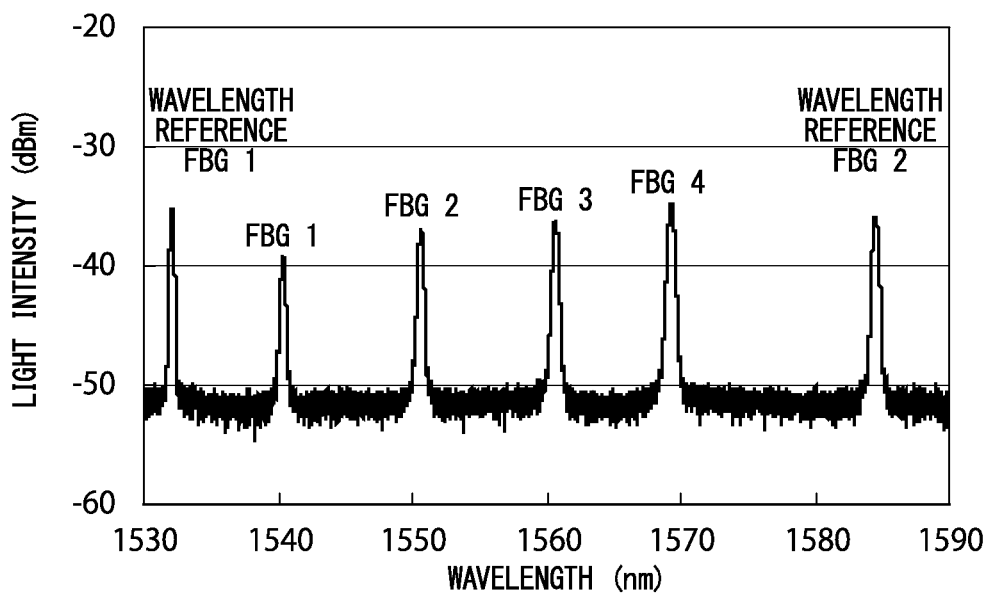
FIG. 6 is a graph that shows the measurement example of the reflection spectrum of the plurality of FBGs used in the exemplary embodiment.

FIG. 6 shows the reflection spectrum of the reference FBGs 1 and 2 and the FBGs 1 to 4 measured by the measuring instrument described above at room temperature (295 K) without strain. As for the Bragg wavelengths of the FBGs 1 to 4 are determined from this reflection spectrum, FBG 1 is 1540.367 nm, FBG 2 is 1550.634 nm, FBG 3 is 1560.660 nm, and FBG 4 is 1569.300 nm.

Figure 7A:
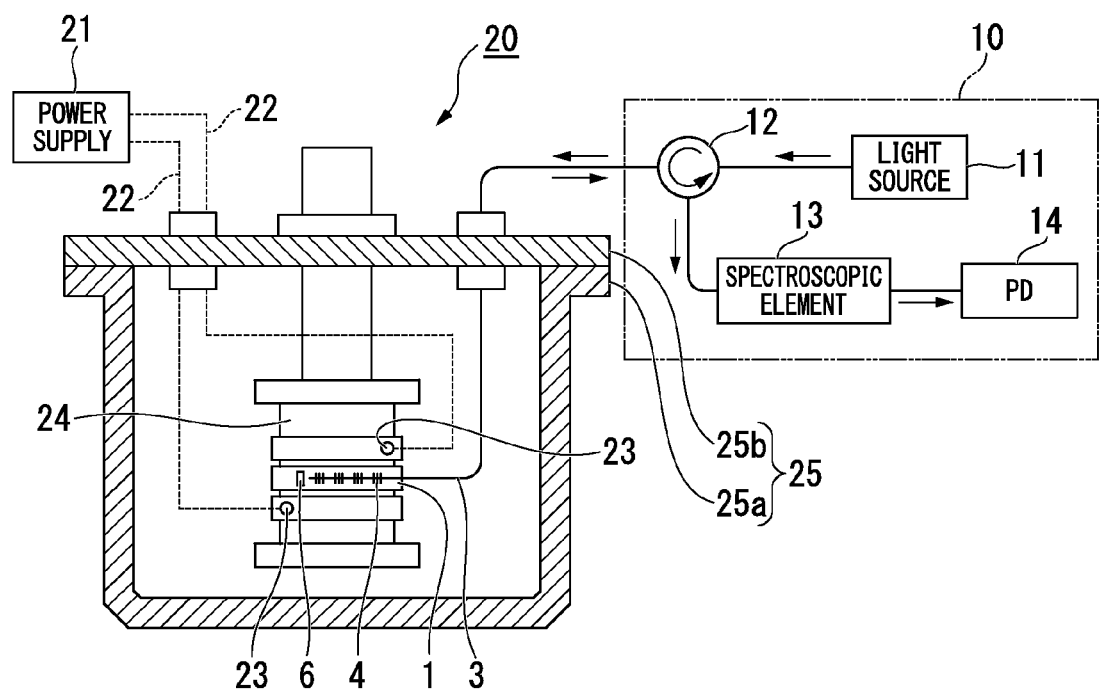
FIG. 7A is a configuration drawing that shows one example of the detection apparatus of the non-superconducting transition used in the present exemplary embodiment.
Figure 7B:
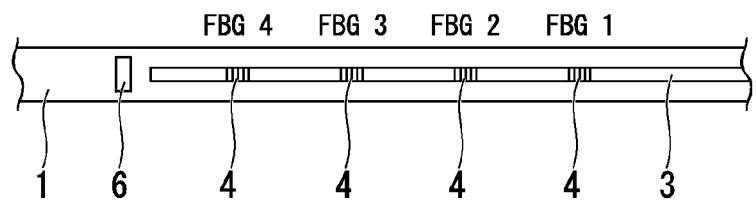
FIG. 7B is a plan view that shows one example of the positional relation of the heater that generates the non-superconducting transition and the FBGs.

FIG. 7A shows the configuration of a testing apparatus 20 used in the present exemplary embodiment. Also, FIG. 7B shows one example of a configuration in which, in the superconducting wire 1 that adhesively attaches the optical fiber 3 with a plurality of fiber Bragg gratings 4 formed therein, a heater 6 for generating the non-superconducting transition of the superconducting wire 1 is provided in the vicinity of the optical fiber 3.

The superconducting wire 1 is fixed in a coil shape to a cylindrical jig 24, and cooled in a low-temperature container 25. The interior of the low-temperature container 25 is sealed by the container body 25a and a lid 25b, and is vacuum-insulated by evacuation using a vacuum pump (not illustrated). Thus, the cooling performance of the refrigerator (not illustrated) in the low-temperature container 25 is enhanced.

Inside the low-temperature container 25, the superconducting wire 1 is cooled to a predetermined temperature using the refrigerator and a semiconductor temperature sensor that is provided in the refrigerator (Cernox thermometer: trade name. Not illustrated).

The optical fiber 3 that is adhesively attached to the superconducting wire 1 is led to outside the low-temperature container 25 via a vacuum feed-through that is capable of coupling optical fibers, and the terminal thereof is connected to the temperature measuring instrument 10. The heater 6 that is provided in the superconducting wire 1 is used for heating the superconducting wire 1. Electrifying the heater 6 raises the temperature of the superconducting wire 1 to the critical temperature of the superconducting layer 1b or higher, whereby it is possible to intentionally generate a non-superconducting transition. Also, electrodes 23 that are provided at both ends of the superconducting wire 1 are connected via a vacuum feed-through that is capable of coupling power cables 22, whereby it is possible to inject a current from the current terminals of the power supply 21 to the superconducting wire 1.

Figure 8:
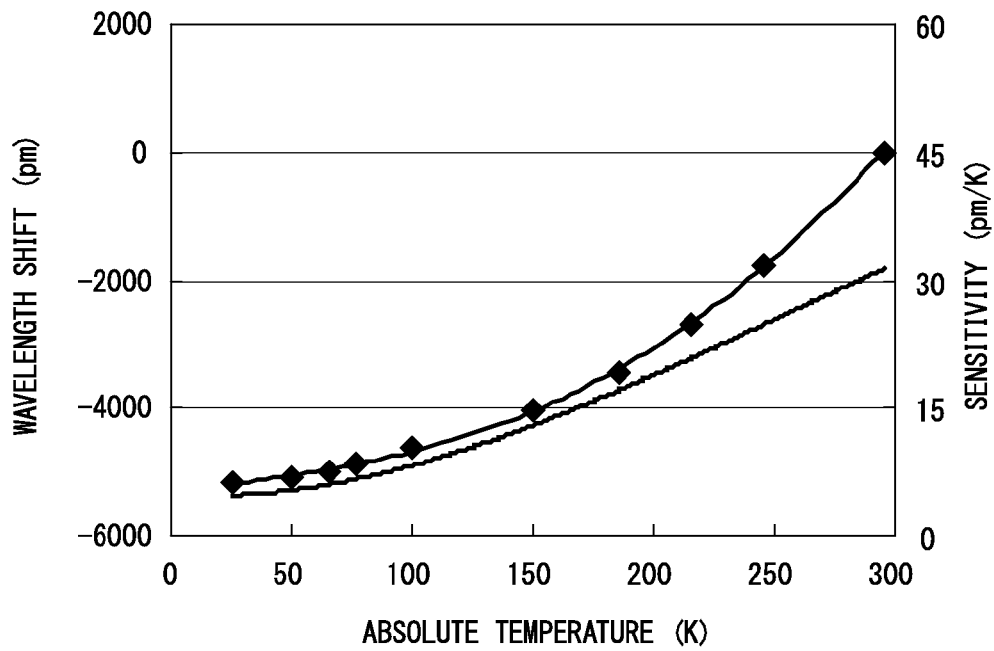
FIG. 8 is a graph that shows a measurement example of a wavelength shift in FBG 1 and the temperature dependency of sensitivity.
Figure 9:
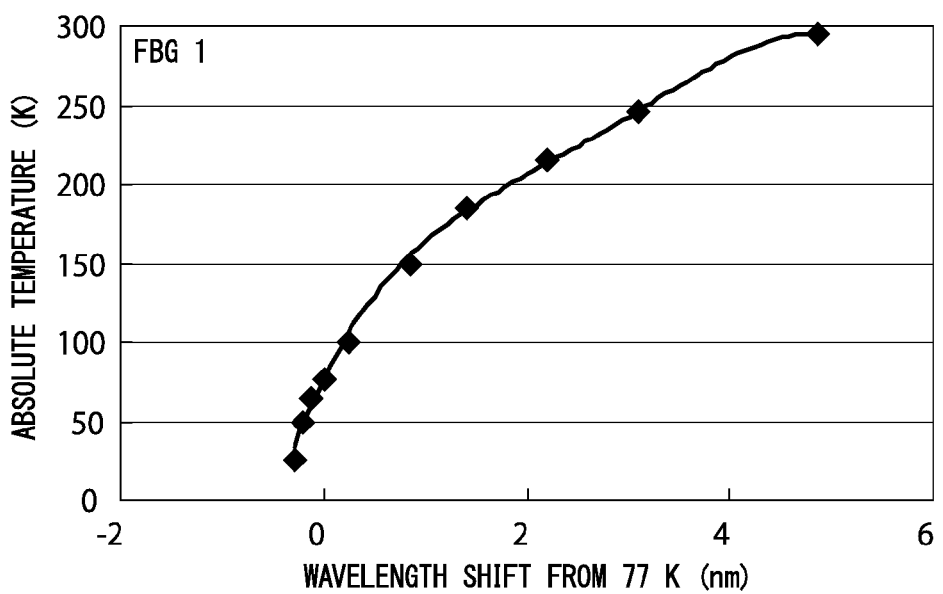
FIG. 9 is a graph that shows a measurement example of the relation between a wavelength shift from 77 K and absolute temperature in FBG 1.
Figure 10:
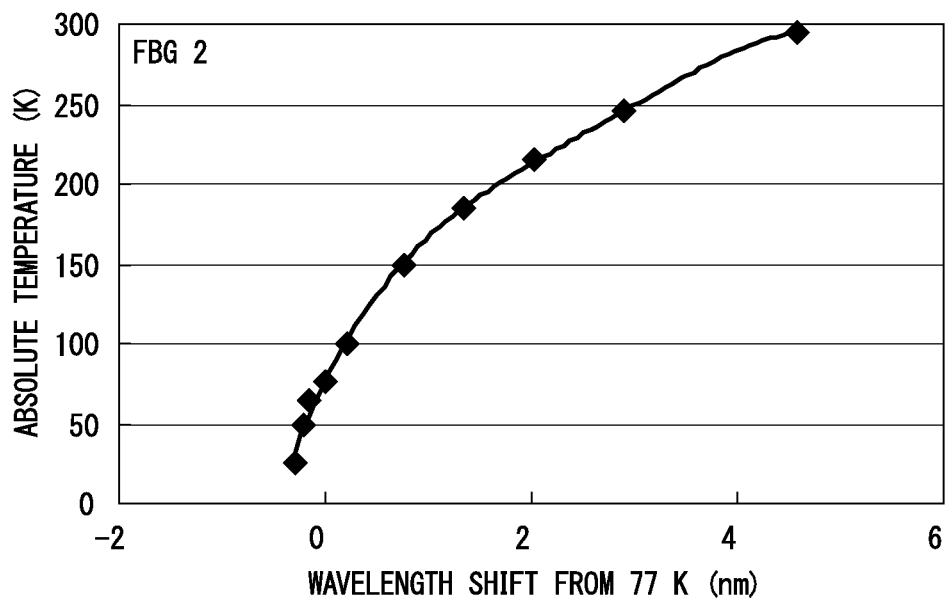
FIG. 10 is a graph that shows a measurement example of the relation between a wavelength shift from 77 K and absolute temperature in FBG 2.
Figure 11:
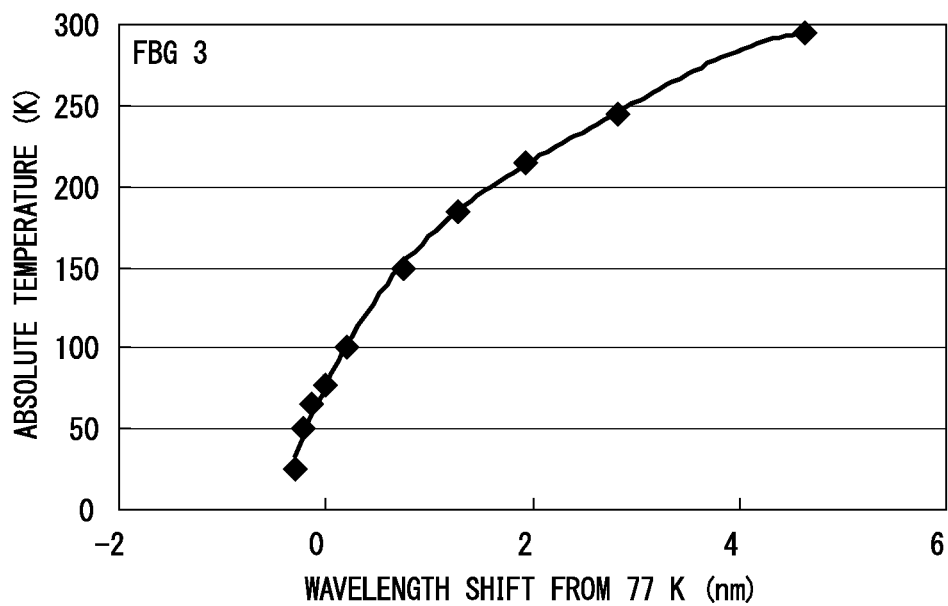
FIG. 11 is a graph that shows a measurement example of the relation between a wavelength shift from 77 K and absolute temperature in FBG 3.
Figure 12:
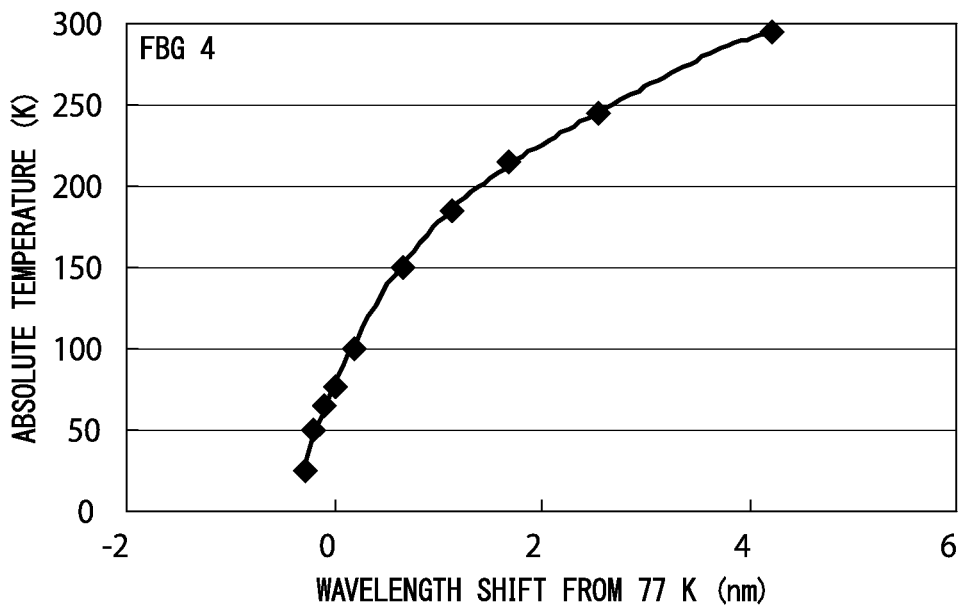
FIG. 12 is a graph that shows a measurement example of the relation between a wavelength shift from 77 K and absolute temperature in FBG 4.

Next, the superconducting wire 1 in the low-temperature container 25 is cooled, the Bragg wavelengths of the FBGs 1 to 4 are measured in the temperature range from 25 K to 295 K, and are determined the relation between the temperature of the superconducting wire 1 and the Bragg wavelength shift from 295K based on the obtained Bragg wavelengths. As a representative example, FIG. 8 shows the relation between the absolute temperature of the FBG 1 and the Bragg wavelength shift, and the sensitivity calculated from the Bragg wavelength shift characteristic (the amount of the Bragg wavelength shift per unit temperature variation). The sensitivity (shown by the line without the symbol (♦) in FIG. 8) is calculated by differentiating with respect to x the result of approximating the relation of the absolute temperature (x) and the Bragg wavelength shift (y) with a fourth-order expression shown in Equation (2). This result can be shown by Equation (3). Note that with regard to the units in Equation (2) and Equation (3), the absolute temperature (x) is K, the wavelength shift (y) is pm, and the sensitivity (y') is pm/K.

[Equation 2]

$$y=-2\times10^{-7}x^4+2\times10^{-4}x^3-8.8\times10^{-3}x^2+4.867x-5303.3 \quad (2)$$

[Equation 3]

$$y'=-8\times10^{-7}x^3+6\times10^{-4}x^2-1.76\times10^{-2}x+4.867 \quad (3)$$

It is confirmed that since the Bragg wavelength monotonically decreases from 295 K to 25K, it is possible to uniquely determine the temperature from the measured Bragg wavelength shift. Also, since the intercept of y' shown by Equation (3) is 4.867, the sensitivity at absolute zero (0 K) is 4.867 pm/K. The fact that the sensitivity at absolute zero is a positive integer indicates that the Bragg wavelength monotonically decreases until absolute zero. That is to say, the temperature measuring method of the present exemplary embodiment can perform measurement until absolute zero.

Next, the relation between absolute temperature and the Bragg wavelength shift obtained by the above experiment is plotted with the wavelength shift from 77 K on the horizontal axis and the absolute temperature on the vertical axis in order to detect the non-superconducting transition at 77 K conducted later. The result in FBGs 1 to 4 is shown in FIGS. 9 to 12. Also, Equations (4) to (7) show the result of approximating these as a fourth-order expression and the correlation function ($R^2$) of this approximate equation. As for the units in Equation (4) to Equation (7), absolute temperature (y) is in K, and wavelength shift (x) is in nm.

[Equation 4]

$$y=-1.3305x^4+14.416x^3-56.067x^2+129.57x+77 \quad (4)$$

($R^2=0.9977$)

[Equation 5]

$$y=-1.1460x^4+12.584x^3-51.552x^2+129.84x+77 \quad (5)$$

($R^2=0.9980$)

[Equation 6]

$$y=-1.1377x^4+12.529x^3-52.127x^2+132.73x+77 \quad (6)$$

($R^2=0.9978$)

[Equation 7]

$$y=-1.3632x^4+14.754x^3-60.766x^2+147.74x+77 \quad (7)$$

($R^2=0.9993$)

Next, the set temperature is substituted into the obtained approximate equation for the FBGs 1 to 4, and the measured temperature and its error are evaluated. The results are shown in Table 1. In any of the FBGs, in the temperature range from 25 to 295 K, the measuring accuracy is ±10 K, and moreover, in the temperature range from 77 to 295 K, a measuring accuracy of ±5 K is obtained. Thereby, in the non-superconducting transition detection at 77 K carried out below, temperature measurement with an accuracy of around ±5 K is considered possible. Note that the reason for obtaining a high measuring accuracy in this manner is that Equations (4) to (7) are approximated by correlation formulas with a high accuracy. That is to say, an extremely high measuring accuracy can be realized in the temperature measurement method of the present exemplary embodiment by determining the relation between the absolute temperature and the Bragg wavelength shift in advance for every FBG, and using an approximate equation determined from this relation.

TABLE 1

| | FBG 1 | | FBG 2 | | FBG 3 | | FBG 4 | |
| --- | --- | --- | --- | --- | --- | --- | --- | --- |
| Set Temperature (K) | Measured Temperature (K) | Error (K) | Measured Temperature (K) | Error (K) | Measured Temperature (K) | Error (K) | Measured Temperature (K) | Error (K) |
| 295 | 295.1 | +0.1 | 295.0 | 0.0 | 294.9 | −0.1 | 294.9 | −0.1 |
| 245 | 246.4 | +1.4 | 245.8 | +0.8 | 245.7 | +0.7 | 245.8 | +0.8 |
| 215 | 210.8 | −4.2 | 213.5 | −1.5 | 213.4 | −1.6 | 212.8 | −2.2 |
| 185 | 183.3 | −1.7 | 185.0 | 0.0 | 184.6 | −0.4 | 185.5 | +0.5 |
| 150 | 155.0 | +5.0 | 151.6 | +1.6 | 152.3 | +2.3 | 152.0 | +2.0 |
| 100 | 105.1 | +5.1 | 101.8 | +1.8 | 102.6 | +2.6 | 103.9 | +3.9 |
| 77 | 77.0 | 0.0 | 77.0 | 0.0 | 77.0 | 0.0 | 77.0 | 0.0 |
| 65 | 60.3 | −4.7 | 56.6 | −8.4 | 59.3 | −5.7 | 63.8 | −1.2 |
| 50 | 47.3 | −2.7 | 46.4 | −3.6 | 44.2 | −5.8 | 47.7 | −2.3 |
| 25 | 34.2 | +9.2 | 32.7 | +7.7 | 34.0 | +9.0 | 29.6 | +4.6 |

Example 2 of Method for Measuring Temperature

In Example 1 of Method for Measuring Temperature described above, the temperatures are calculated using the approximate equations, each of which is determined for each FBG. However, the temperatures may also be calculated using one approximate equation provided in advance. Table 2 is the result of calculating the temperatures using the aforementioned Equations (4) to (7) with respect to a wavelength shift of FBG 1. Since Equation (4) is a relational expression of the absolute temperature and the Bragg wavelength shift obtained by experiment using FBG 1, it is the same result as Table 1. In addition, even if Equations (5) to (7) obtained by experiment using FBGs 2 to 4 are used, a measuring accuracy of ±20 K is obtained in a temperature range from 25 to 295 K.

TABLE 2

| Set Temperature (K) | Equation (4) | | Equation (5) | | Equation (6) | | Equation (7) | |
|---|---|---|---|---|---|---|---|---|
| | Measured Temperature (K) | Error (K) | Measured Temperature (K) | Error (K) | Measured Temperature (K) | Error (K) | Measured Temperature (K) | Error (K) |
| 295 | 295.1 | +0.1 | 295.8 | +0.8 | 294.6 | −0.4 | 293.7 | −1.3 |
| 245 | 246.4 | +1.4 | 253.1 | +8.1 | 255.6 | +10.6 | 264.6 | +19.6 |
| 215 | 210.8 | −4.2 | 218.0 | +3.0 | 221.2 | +6.2 | 230.8 | +15.8 |
| 185 | 183.3 | −1.7 | 188.3 | +3.3 | 191.1 | +6.1 | 200.4 | +15.4 |
| 150 | 155.0 | +5.0 | 157.5 | +7.5 | 159.5 | +9.5 | 167.3 | +17.3 |
| 100 | 105.1 | +5.1 | 105.4 | +5.4 | 106.0 | +6.0 | 109.2 | +9.2 |
| 77 | 77.0 | 0.0 | 77.0 | 0.0 | 77.0 | 0.0 | 77.0 | 0.0 |
| 65 | 60.3 | −4.7 | 60.4 | −4.6 | 60.0 | −5.0 | 58.0 | −7.0 |
| 50 | 47.3 | −2.7 | 47.5 | −2.5 | 46.9 | −3.1 | 43.3 | −6.7 |
| 25 | 34.2 | +9.2 | 34.5 | +9.5 | 33.6 | +8.6 | 28.5 | +3.5 |

Figure 13:
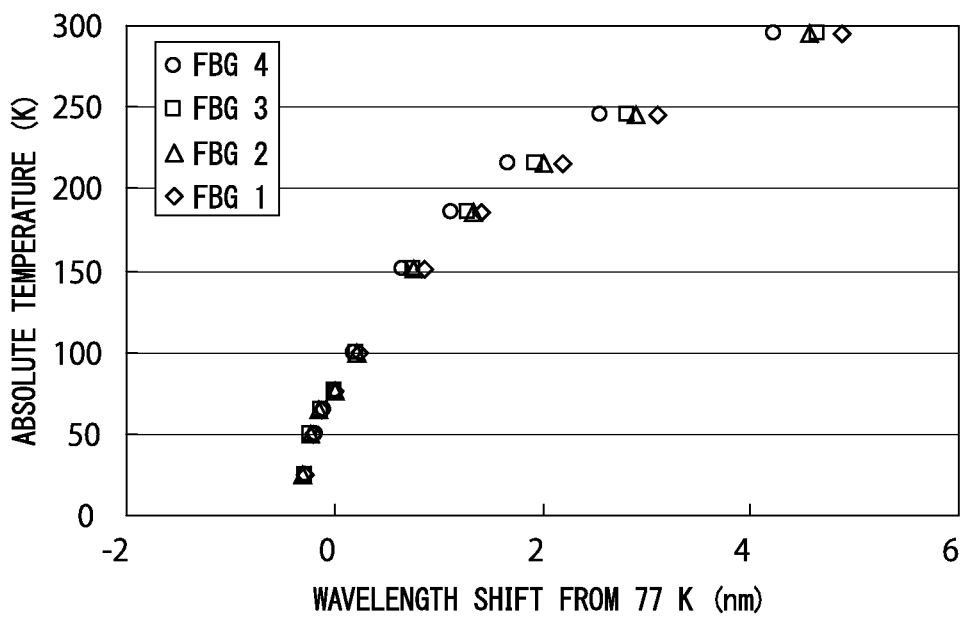
FIG. 13 is a graph that plots in a superimposed manner the relations between a wavelength shift from 77 K and absolute temperature shown in FIGS. 9 to 12.

FIG. 13 is a drawing that plots in a single graph the result of the aforementioned FIGS. 9 to 12. It shows that for the FBGs 1 to 4, the relations of the Bragg wavelength shift to a temperature variation are extremely close. Also, in the detection of non-superconducting transition at 77 K carried out below, it is considered to have a temperature measuring accuracy of around ±20 K. Although the temperature accuracy is inferior compared to the case of calculating with the approximate equation obtained for each FBG of the aforementioned (Exemplary Embodiment 1 of Method for Measuring Temperature), by using one approximate equation provided in advance, there is no longer a need to calculate in advance the relation between the absolute temperature and the Bragg wavelength shift for each FBG. Therefore, the method is also useful.

[Example 1 of Method for Detecting Non-Superconducting Transition]

Next, using the testing apparatus shown in FIG. 7A and FIG. 7B, a non-superconducting transition is intentionally generated in the superconducting wire 1 of the present example, and detection of the non-superconducting transition by FBGs and measurement of the temperature that occurs at this time are conducted.

Figure 14:
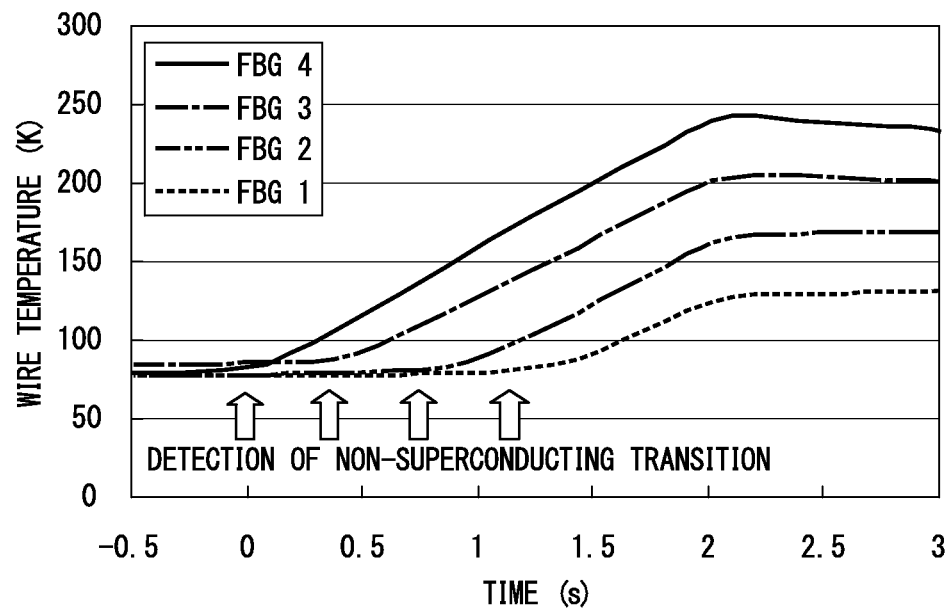
FIG. 14 is a graph that shows a measurement example of the temperature variation of each FBG in Exemplary Embodiment 1 of the method for detecting the non-superconducting transition.

FIG. 14 is the measurement result of the wire temperature from the FBGs 1 to 4 when, the temperature of the superconducting wire 1 is cooled at 77 K, which is under the critical temperature of the superconducting layer, and injecting 160 A of electrical current through the superconducting layer, energizing the heater 6 for 3 seconds to locally heat the superconducting wire 1.

The FBG 4, which is close to the heater 6, detects the heat generation the earliest, and FBG 1, which is far from the heater 6, detects the heat generation the latest. Note that in the present example, the time that FBG 4, which is close to the heater 6, detects the heat generation is defined as 0 sec, and at the point of 2.1 sec, at which time has sufficiently elapsed after detection of the heat generation by the FBG 1 that is far from the heater 6, the current injection to the superconducting wire 1 is shut off. This result indicates that the non-superconducting transition that is produced by the heater 6 propagates in the longitudinal direction of the superconducting wire 1. Also, the detection time difference of the each FBG indicates the propagation rate of the non-superconducting transition, and the slope of the wire temperature variation indicates the temperature increasing rate.

The propagation rate obtained from this result is approximately 25 mm/sec, and the temperature increasing rate is approximately 80 K/sec. From these rates, it is possible to determine the maximum temperature that occurs at the starting point of the non-superconducting transition, that is to say, at the center of the heater 6, using Equation (8). Note that 10 mm in Equation (8) is the distance between the FBG 4 and the heater 6, and 245 K is the maximum temperature measured by the FBG 4 shown in FIG. 14. The result of Equation (8) is 277 K, and since the temperature measuring accuracy in the range of 77 to 295 K is evaluated in advance is ±5 K, the maximum temperature that occurs in the wire can be estimated as being approximately 277±5 K.

[Equation 8]

$$\frac{10 \text{ (mm)}}{25 \text{ (mm/s)}} \times 80 \text{ (K/s)} + 245(K) = 277(K) \quad (8)$$

As described above, according to the present exemplary embodiment, it is possible to measure the propagation rate of the non-superconducting transition and the temperature increasing rate of the superconducting wire. Also, from these rates, it is possible to measure the maximum temperature at the starting point of the non-superconducting transition, that is to say, the maximum temperature that occurs in this superconducting wire. From a comparison of this maximum temperature and the safety-standard temperature that is set in advance, it is possible to determine the necessity of inspection/repair of this superconducting wire.

[Example 2 of Method for Detecting Non-Superconducting Transition]

Using the configuration of Exemplary Embodiment 1, the heater 6 was energized for 1.5 sec.

Figure 15:
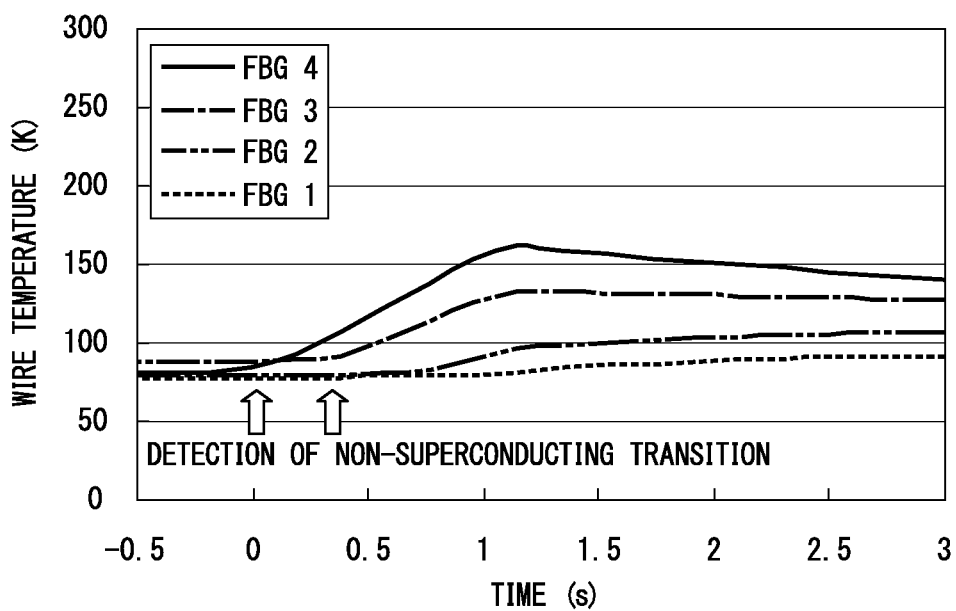
FIG. 15 is a graph that shows a measurement example of the temperature variation of each FBG in Exemplary Embodiment 2 of the method for detecting the non-superconducting transition.

FIG. 15 is the result of measuring the wire temperature using the FBGs when locally heating the superconducting wire 1 by energizing the heater for 1.5 sec. Note that in the present exemplary embodiment, the time that FBG 4 detects heat generation is defined as 0 sec, and at the point of 1.1 sec, the injected electrical current of the superconducting wire 1 is shut off. The temperature increasing rate is approximately 80 K/s at FBG 4, approximately 65 K/s at FBG 3, approximately 40 K/s at FBG 2, and approximately 15 K/s at FBG 1.

Since FBG 4 and FBG 3 that are close to the heater indicate a large temperature increasing rate similarly to Exemplary Embodiment 1, it is confirmed that the non-superconducting transition is propagated to the positions of the FBG 4 and FBG 3. Since the temperature increasing rate is smaller at the FBG 2 and FBG 1 that are far from the heater, it is possible to determine that the temperature increases caused by the thermal conduction from the FBG 4 and FBG 3 portions that have transitioned to a non-superconducting state, not by heat generation due to the non-superconducting transition.

From this result, the range that indicates a non-superconducting transition in the present exemplary embodiment is from the center of the heater to the FBG 3, and that distance can be estimated as 20 mm. Note that since this non-superconducting transition is considered to propagate at a uniform rate in both directions from the starting point along the longitudinal direction of the wire, the range that actually transitions to non-superconducting state can be estimated to be approximately 40 mm.

As described above, according to the present exemplary embodiment, it is possible to detect the range of the non-superconducting transition. Accordingly, even when inspection or repair of the superconducting wire is required, it is possible to limit the range thereof, and possible to improve the work efficiency. In addition, when Exemplary Embodiment 2 is compared with Exemplary Embodiment 1, after any one FBG (FBG 4) has detected heat generation, by shutting off the current that is injected to the superconducting wire 1 at an early stage, it is possible to reduce the maximum temperature that is generated in the superconducting wire and the range of the non-superconducting transition. That is to say, by providing a control device that controls the amount of injection current to the superconducting wire by regulating (lowering) or shutting off (stopping) the current in the case of detecting a temperature abnormality, an alarm device that gives an alarm to the operator in the case of detecting the abnormality, a display device for the running state, a recording device of the temperature history, and the like, it can be utilized as a protective device of the superconducting wire.

[Example 3 of Method for Detecting Non-Superconducting Transition]

Using the configuration of Example 1, the injected electrical current of the superconducting wire is changed.

Figure 16:
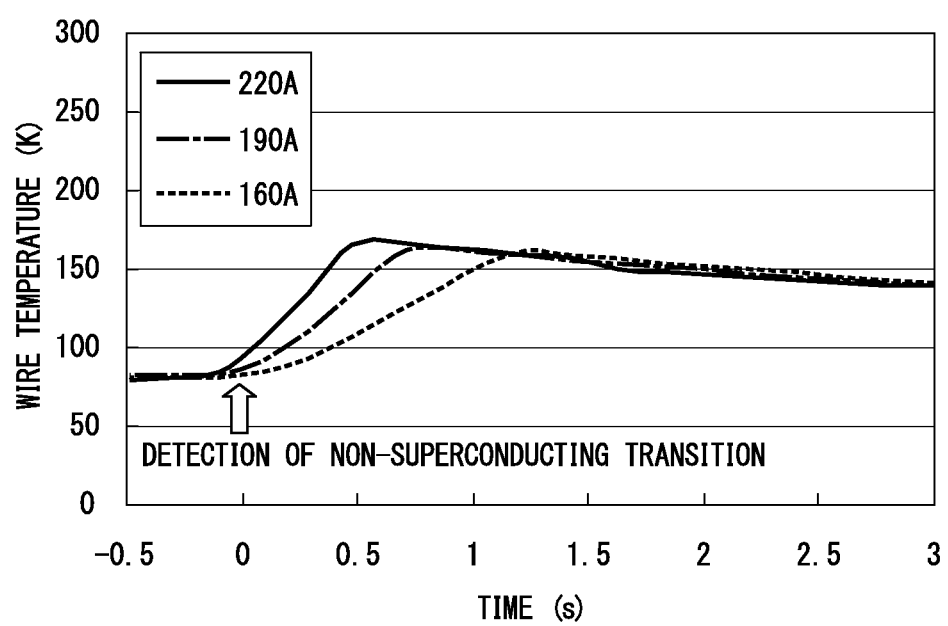
FIG. 16 is a graph that shows a measurement example of the temperature variation of FBG 4 in Exemplary Embodiment 3 of the method for detecting the non-superconducting transition.

FIG. 16 is a graph that shows the change over time of the wire temperature measured by the FBG 4, with the injected electrical current of the superconducting wire changed to 160 A, 190 A, 220 A, when the heater is energized for 1.5 sec. In FIG. 16, the plot for 160 A cites the result of Example 2 (FIG. 15). Note that in the present example, the time that FBG 4 detects heat generation is defined as 0 sec, and at the point of this FBG reaching 150 K or more, the injected electrical current of the superconducting wire 1 is shut off. The temperature increasing rate is approximately 80 K/sec at 160 A, approximately 140 K/sec at 190 A, and approximately 160 K/sec at 220 A.

Figure 17:
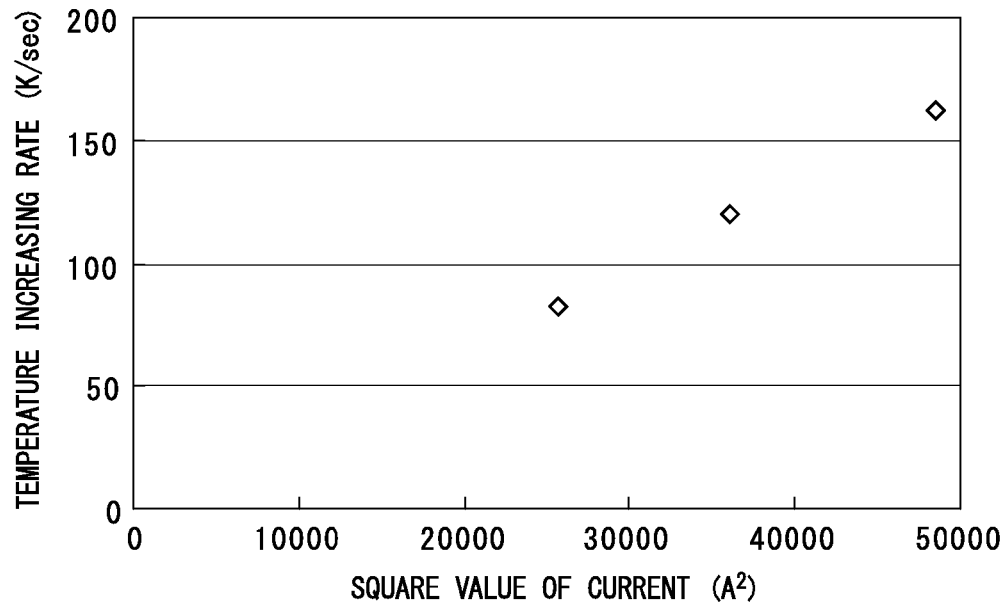
FIG. 17 is a graph that shows the relation between the square value of the injected electrical current of the superconducting wire and the temperature increasing rate in Exemplary Embodiment 3 of the method for detecting the non-superconducting transition.

FIG. 17 is a graph that shows the relation between the square value of the injected electrical current of the superconducting wire 1 and the temperature increasing rate. The temperature increasing rate increases nearly in direct proportion to the square value of the injected electrical current of the superconducting wire 1. In a superconducting wire that has transitioned to non-superconducting state, assuming all amount of the injected current (having a current value of I) flows through the metal stabilization layer (having a resistance value of R), Joule heat that is produced in direct proportion to $R \times I^2$. That is to say, the fact that the temperature increasing rate is in direct proportion to the square value of the electrical current flowing through the superconducting wire is originated from Joule heat that is generated in the metal stabilization layer at the non-superconducting transition portion.

For this reason, when judging whether or not the non-superconducting transition has propagated in the aforementioned Example 2 of the method for detecting a non-superconducting transition, it is necessary to take into consideration that the injected current to the superconducting wire causes larger temperature increasing rate due to the non-superconducting transition.

Note that in FIG. 16, the highest temperature measured at the FBG 4 is to the same extent as approximately 160 to 170 K. However, when estimating the highest temperature at the starting point 2 in the same way as the aforementioned (Exemplary Embodiment 1 of the method for detecting a non-superconducting transition), the higher current condition results in the highest temperature at the starting point.

As described above, according to the present invention, it is possible to qualitatively know the mechanism of heat generation accompanying the non-superconducting transition of the superconducting wire. It is also possible to quantitatively measure the temperature increasing rate and the maximum temperature at this time.

In Examples 1 to 3 described above, the superconducting wire 1 has been fixed in a coil shape. However, the present example is not limited to these Examples. For example, by making the superconducting wire into a cable, it can also be used for a superconducting cable that transmits large currents.

[Example 4 of Method for Detecting Non-Superconducting Transition]

Using the configuration of Example 1, the superconducting wire 1 is cooled at 50 K, and a magnetic field of 3 T is applied to an electromagnet (not illustrated) provided on the outer circumference of the superconducting wire 1. The critical current of the superconducting wire 1 at 50 K and 3 T is 200 A. In the present example, by injecting current to the superconducting wire 1, it is possible to generate electromagnetic force (hoop stress).

Figure 18:
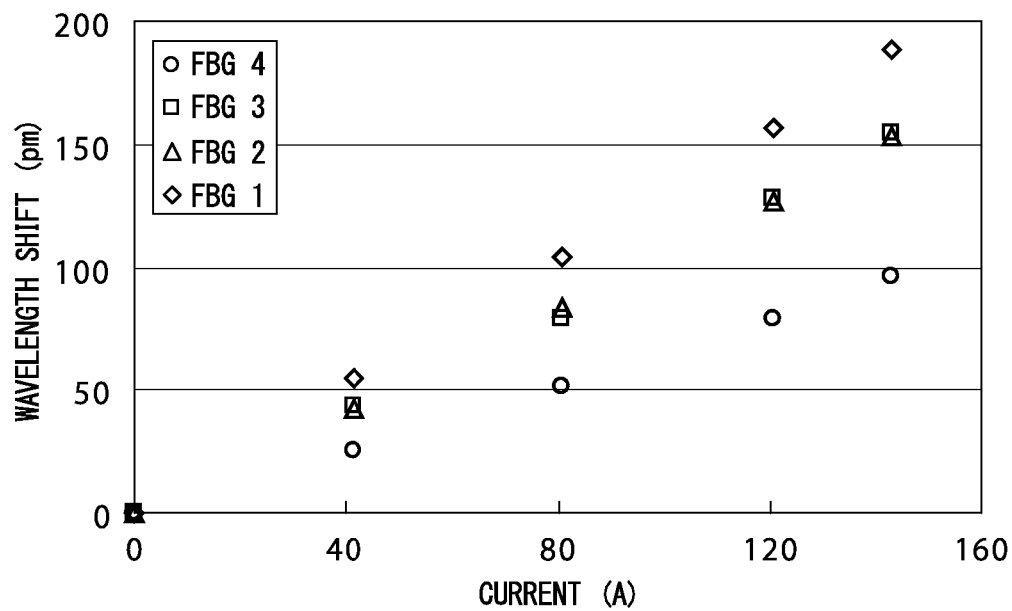
FIG. 18 is a graph that shows the relation between the injected electrical current of the superconducting wire and the wavelength shift of each FBG in Exemplary Embodiment 4 of the method for detecting the non-superconducting transition.

FIG. 18 is a graph that shows the Bragg wavelength shift of FBGs 1 to 4 when changing the injected current value of the superconducting wire 1 to 40 A, 80 A, 120 A, and 140 A. When hoop stress is generated, since tensile strain is induced in the longitudinal direction of the superconducting wire 1, the tensile strain is transferred to the FBGs 1 to 4. Accordingly, the lattice interval $\Lambda$ of the FBG is stretched, and the Bragg wavelength $\lambda_B$ shifts to the longer wavelength. With regard to a variation in the injected current value of the superconducting wire 1 and the Bragg wavelength shift, although there is a slight difference among the FBGs 1 to 4, it has been confirmed that the Bragg wavelength shift is directly proportional to the injected current value of the superconducting wire 1.

Figure 19:
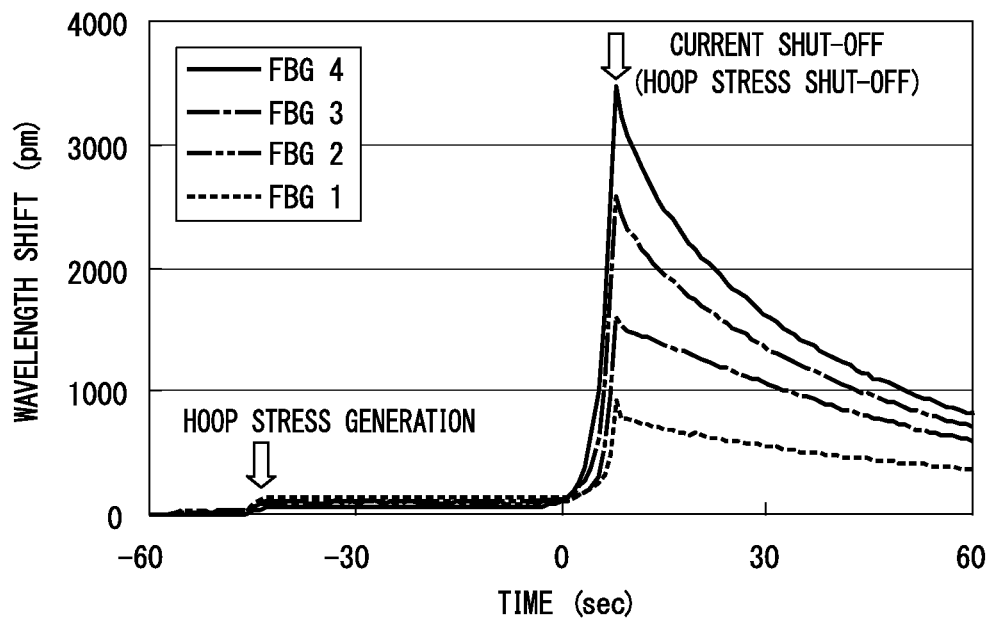
FIG. 19 is a graph that shows the wavelength shift of each FBG in Exemplary Embodiment 4 of the method for detecting the non-superconducting transition.
Figure 20:
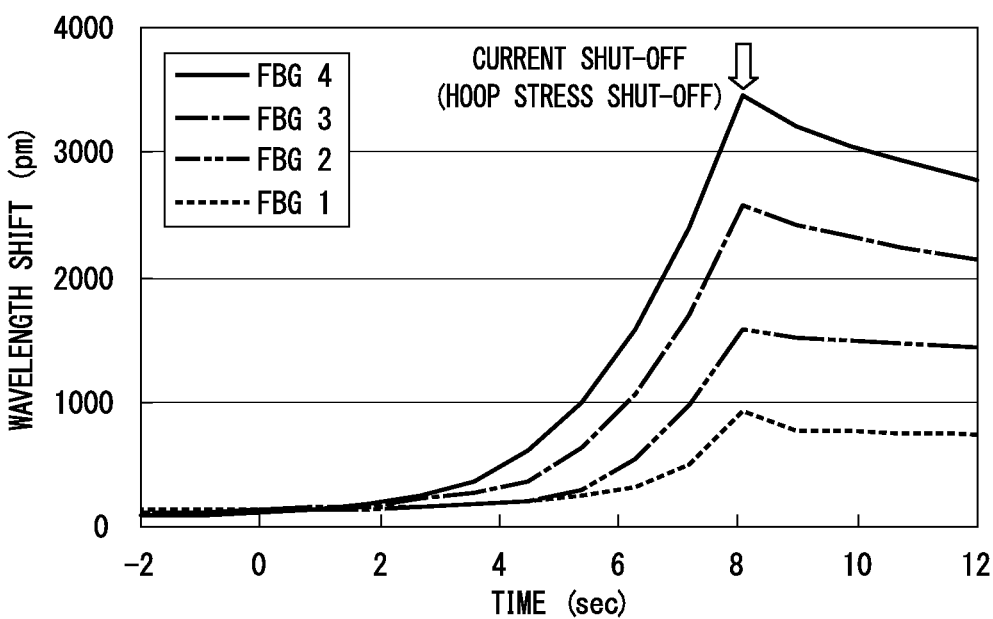
FIG. 20 is a graph that shows the wavelength shift of each FBG in the section of −2 to 12 sec of Exemplary Embodiment 4 of the method for detecting the non-superconducting transition.

Next, the injected current of the superconducting wire 1 is once shut off, and after a certain time has elapsed, 100 A is once again applied to the superconducting wire 1, and the hoop stress is generated. After generating the hoop stress, and moreover after a certain time has elapsed, the heater 6 is energized for 5 sec to locally heat the superconducting wire 1. FIG. 19 is the measurement result of the Bragg wavelength shifts for the FBGs 1 to 4 at this time. Also, FIG. 20 is a graph that enlarges the section of −2 to 12 sec in FIG. 19. Note that in the present example, the time that the Bragg wavelength of FBG 4 shifts greatly (detects the heat generation) is defined as 0 sec, and at the point in time of 8 sec, the injected current of the superconducting wire 1 is shut off.

Figure 21:
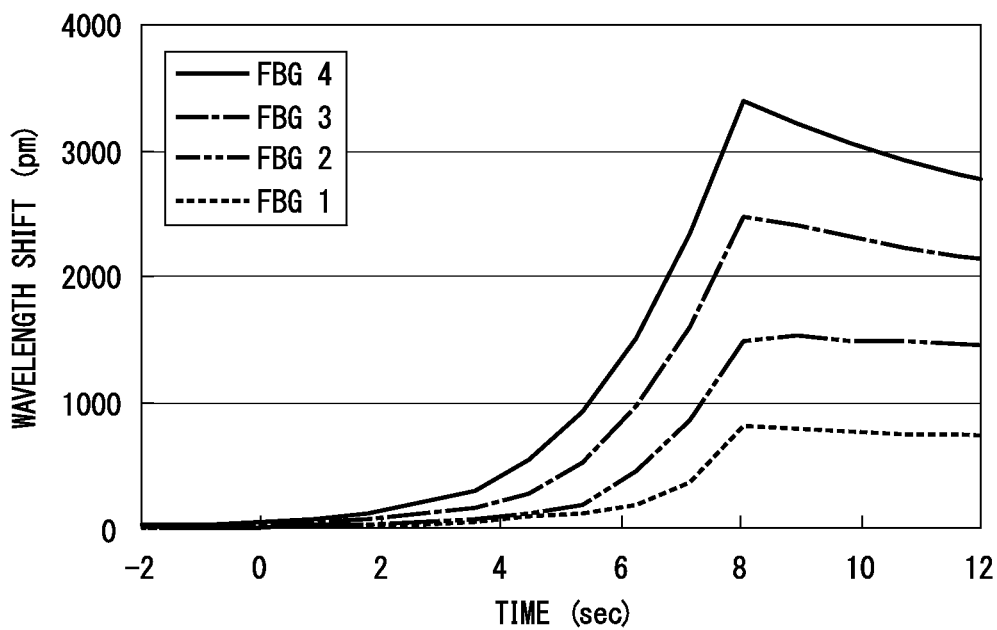
FIG. 21 is a graph that subtracts the wavelength shift due to electromagnetic force from the wavelength shift of each FBG in the section of −2 to 12 sec of Exemplary Embodiment 4 of the method for detecting the non-superconducting transition, and determines the wavelength shift due to the temperature variation.

In FIG. 19, when the hoop stress is generated by injecting the current of 100 A to the superconducting wire 1 from the point of −45 sec, it can be confirmed that the wavelength shift on the vertical axis increases, and the Bragg wavelength of the FBGs 1 to 4 shifts to the longer wavelength. Also, the wavelength shifts due to this hoop stress are almost constant in the section before the FBGs detect the heat generation (in FIG. 19, −45 sec to approximately 0 sec). Moreover, it is confirmed that these wavelength shifts correspond to the wavelength shift for the current of 100 A in FIG. 18. Since this hoop stress disappears when the injected current is shutting off, only in the section from −45 sec to 8 sec, the temperature variation induced in the superconducting wire 1 and the Bragg wavelength shift due to the hoop stress are measured. Accordingly, when the obtained Bragg wavelength shift is converted as a temperature, since the Bragg wavelength shift due to the hoop stress also ends up being converted as a temperature variation, it is preferable to determine the temperature variation induced in the superconducting wire 1 by subtracting the Bragg wavelength shift due to the hoop stress in advance. In the present example, the Bragg wavelength shift of the section from −30 sec to −10 sec in which heat generation of the FBGs 1 to 4 is not clearly recognized for each FBG, and this value is subtracted only for the section from −45 sec to 8 sec. FIG. 21 shows the result of the Bragg wavelength shift that subtracts the Bragg wavelength shift due to the hoop stress. Thereby, it is possible to accurately determine the temperature variation produced in the superconducting wire 1 without converting the Bragg wavelength shift due to the hoop stress as a temperature variation.

Next, the temperature of the superconducting wire 1 is estimated based on the Bragg wavelength shift obtained in FIG. 21. The relations of the wavelength shift and the absolute temperature from 50 K is calculated from the relation of the absolute temperature and the Bragg wavelength shift obtained in advance in Example 1, and the results of approximating as a fourth-order equation and the correlation expression ($R^2$) of these approximate equations are shown in Equations (9) to (12). Note that with regard to the units in Equation (9) to Equation (12), the absolute temperature (y) is K, and the wavelength shift (x) is nm.

[Equation 9]

$$y = -0.8197x^4 + 10.381x^3 - 49.342x^2 + 138.44x + 50 \quad (9)$$

($R^2 = 0.9972$)

[Equation 10]

$$y = -0.9853x^4 + 11.872x^3 - 53.978x^2 + 145.57x + 50 \quad (10)$$

($R^2 = 0.9975$)

[Equation 11]

$$y = -0.5806x^4 + 8.0515x^3 - 43.565x^2 + 138.56x + 50 \quad (11)$$

($R^2 = 0.9963$)

[Equation 12]

$$y = -0.7443x^4 + 10.365x^3 - 54.55x^2 + 158.32x + 50 \quad (12)$$

($R^2 = 0.9989$)

Figure 22:
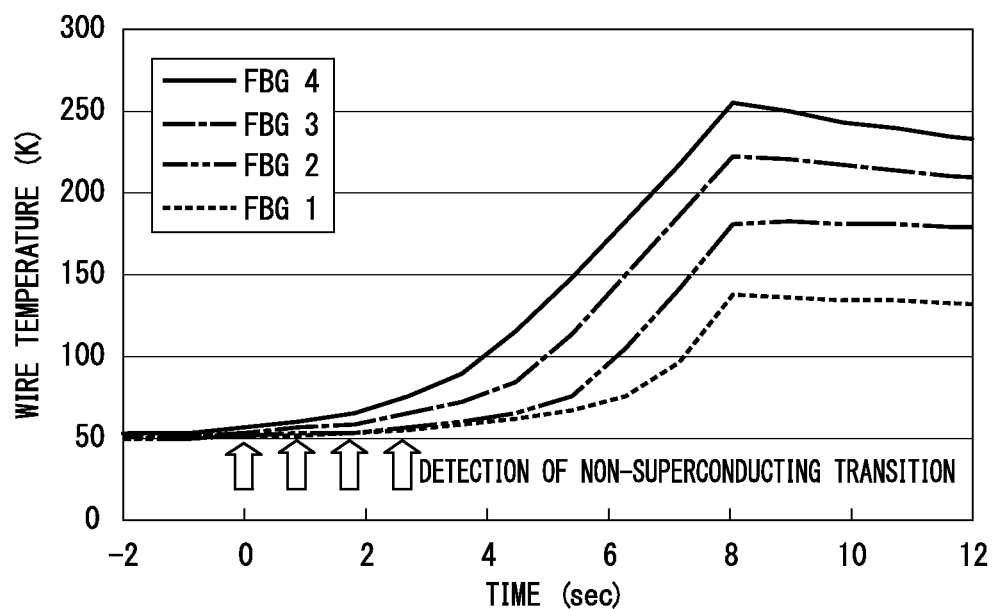
FIG. 22 is a graph that shows a measurement example of the wavelength shift of each FBG in the section of −2 to 12 sec of Exemplary Embodiment 4 of the method for detecting the non-superconducting transition.

Using the Equations (9) to (12) obtained above, the Bragg wavelength shifts obtained in FIG. 21 is converted to a temperature of the superconducting wire 1. FIG. 22 is a graph that shows the result of converting it to a temperature of the superconducting wire 1. It is possible to accurately determine the temperature variation induced in the superconducting wire 1 without converting the Bragg wavelength shift due to the hoop stress as the temperature. The propagation rate obtained from this result is approximately 11 mm/sec, and the temperature increasing rate is approximately 25 K/sec. By substituting these rates and the maximum temperature of 256 K measured by FBG 4 into the above general equation (L/V)υ+Tmax and calculating in the same manner as Equation (8), the maximum temperature induced in the superconducting wire 1 is estimated as 284 K as shown by Equation (13).

[Equation 13]

$$\frac{10 \text{ (mm)}}{11 \text{ (mm/s)}} \times 25 (\text{K/s}) + 256 (\text{K}) = 284 (\text{K}) \quad (13)$$

In the present exemplary embodiment, the electromagnetic forced (hoop stress) is generated by an electromagnetic provided on the outer periphery of the superconducting wire 1. However, it is also possible to utilize the present invention even in the case of generating hoop stress by manufacturing a large coil using a long-length superconducting wire and applying current to the large coil.

What is claimed is:

1. A method for detecting a non-superconducting transition of a superconducting wire comprising a substrate, a superconducting layer that has a critical temperature of 77 K or more, and a metal stabilization layer, the method comprising:
    adhesively attaching an optical fiber in which a plurality of fiber Bragg gratings are formed in a core along a longitudinal direction thereof to the superconducting wire;
    concentrically winding the superconducting wire adhesively attached with the optical fiber in which the fiber Bragg gratings are formed;
    fixing the wound superconducting wire in a coil shape;
    after the fixing, measuring in advance a Bragg wavelength shift of the fiber Bragg gratings with respect to a temperature variation of the superconducting wire, and determining a relational expression based on the Bragg wavelength shift for a temperature calculation of the superconducting wire;
    measuring the temperature variation of the fiber Bragg gratings continuously from before to after the non-superconducting transition occurs in the superconducting wire;
    determining temperature variations of the plurality of fiber Bragg gratings before and after the non-superconducting transition of the superconducting wire using the relational expression; and
    calculating a propagation rate of the non-superconducting transition based on both a time difference of temperature increases of the plurality of fiber Bragg gratings, and an interval between each of the fiber Bragg gratings.

2. The method for detecting a non-superconducting transition of a superconducting wire according to claim 1, further comprising:
measuring a maximum temperature Tmax measured at any of the plurality of fiber Bragg gratings, a distance L between the fiber Bragg grating where the maximum temperature Tmax is measured and the starting point of the non-superconducting transition, a temperature increasing rate u of the fiber Bragg g rating where the maximum temperature Tmax is measured, and a propagation rate V of the non-superconducting transition; and
calculating a maximum temperature at a starting point of the non-superconducting transition that equals to (LV) υ+Tmax.

3. The method for detecting a non-superconducting transition of a superconducting wire according to claim 2, further comprising:
measuring the maximum temperature Tmax and the temperature increasing rate υ using the fiber Bragg grating closest to the starting point of the non-superconducting transition.

4. The method for detecting a non-superconducting transition of a superconducting wire according to claim 3, further comprising:
determining the temperature increasing rate of the respective fiber Bragg gratings based on the temperature variation of the respective fiber Bragg gratings; and
determining that the non-superconducting transition is propagated to a position of the fiber Bragg grating when the temperature increasing rate is equal to or greater than a predetermined threshold value.

5. The method for detecting a non-superconducting transition of a superconducting wire according to claim 4, wherein
the predetermined threshold value is set in advance based on a value of an injected current of the superconducting wire.

6. The method for detecting a non-superconducting transition of a superconducting wire according to claim 2, further comprising:
determining the temperature increasing rate of the respective fiber Bragg gratings based on the temperature variation of the respective fiber Bragg gratings; and
determining that the non-superconducting transition is propagated to a position of the fiber Bragg grating when the temperature increasing rate is equal to or greater than a predetermined threshold value.

7. The method for detecting a non-superconducting transition of a superconducting wire according to claim 6, wherein
the predetermined threshold value is set in advance based on a value of an injected current of the superconducting wire.

8. The method for detecting a non-superconducting transition of a superconducting wire according to claim 1, further comprising:
determining the temperature increasing rate of the respective fiber Bragg gratings based on the temperature variation of the respective fiber Bragg gratings; and
determining that the non-superconducting transition is propagated to a position of the fiber Bragg grating when the temperature increasing rate is equal to or greater than a predetermined threshold value.

9. The method for detecting a non-superconducting transition of a superconducting wire according to claim 8, wherein
the predetermined threshold value is set in advance based on a value of an injected current of the superconducting wire.

10. The method for detecting a value of an injected current transition of a superconducting wire according to claim 1, the method further comprising:
after the fixing, measuring in advance a Bragg wavelength shift of the fiber Bragg gratings due to electromagnetic force generated by the superconducting wire; and
determining the temperature variation of the plurality of fiber Bragg gratings before and after the non-superconducting transition of the superconducting wire, using a Bragg wavelength shift in the relational expression, the Bragg wavelength shift being obtained by subtracting the Bragg wavelength shift of the fiber Bragg gratings due to the electromagnetic force.

11. The method for detecting a non-superconducting transition of a superconducting wire according to claim 1, wherein the optical fiber in which a plurality of fiber Bragg gratings are formed is connected to a temperature measuring instrument,
the temperature measuring instrument comprising, a broadband light source, a spectroscopic element, an optical device where measurement light from the broadband light source enters and that makes Bragg reflection light from the plurality of fiber Bragg gratings is entered the spectroscopic element, and a light receiving element that detects a light dispersed by the spectroscopic element and outputs a voltage signal.

12. A method for detecting a non-superconducting transition of a superconducting wire comprising a substrate, a superconducting layer that has a critical temperature of 77 K or more, and a metal stabilization layer, the method comprising:
adhesively attaching an optical fiber in which a plurality of fiber Bragg gratings are formed in a core along a longitudinal direction thereof to the superconducting wire;
concentrically winding the superconducting wire adhesively attached with the optical fiber in which the fiber Bragg gratings are formed;
fixing the wound superconducting wire in a coil shape;
after the fixing, measuring in advance a Bragg wavelength shift of the fiber Bragg gratings with respect to a temperature variation of the superconducting wire, and determining a relational expression based on the Bragg wavelength shift for a temperature calculation of the superconducting wire;
measuring the temperature variation of the fiber Bragg gratings continuously from before to after the non-superconducting transition occurs in the superconducting wire;
determining temperature variations of the plurality of fiber Bragg gratings before and after the non-superconducting transition using the relational expression;
determining the temperature increasing rate of the respective fiber Bragg gratings based on the temperature variation of the respective fiber Bragg gratings; and
determining whether or not the non-superconducting transition is propagated to a position of the fiber Bragg grating based on whether or not the temperature increasing rate is equal to or greater than a predetermined threshold value.

13. The method for detecting a non-superconducting transition of a superconducting wire according to claim 12, further comprising:
measuring a distance between a starting point of the non-superconducting transition and a farthest fiber Bragg grating from the starting point among the fiber Bragg gratings which are determined that the non-superconducting transition is propagated to the fiber Bragg gratings; and
estimating a range of the non-superconducting transition by doubling the measured distance.

14. The method for detecting a non-superconducting transition of a superconducting wire according to claim 13, wherein
the predetermined threshold value is set in advance based on a value of an injected current of the superconducting wire.

15. The method for detecting a non-superconducting transition of a superconducting wire according to claim 12, wherein
the predetermined threshold value is set in advance based on a value of an injected current of the superconducting wire.

16. The method for detecting a value of an injected current transition of a superconducting wire according to claim 12, the method further comprising:
after the fixing, measuring in advance a Bragg wavelength shift of the fiber Bragg gratings due to electromagnetic force generated by the superconducting wire; and
determining the temperature variation of the plurality of fiber Bragg gratings before and after the non-superconducting transition of the superconducting wire, using a Bragg wavelength shift in the relational expression, the Bragg wavelength shift being obtained by subtracting the Bragg wavelength shift of the fiber Bragg gratings due to the electromagnetic force.

17. The method for detecting a non-superconducting transition of a superconducting wire according to claim 12, wherein the optical fiber in which a plurality of fiber Bragg gratings are formed is connected to a temperature measuring instrument,
the temperature measuring instrument comprising, a broadband light source, a spectroscopic element, an optical device where measurement light from the broadband light source enters and that makes Bragg reflection light from the plurality of fiber Bragg gratings is entered the spectroscopic element, and a light receiving element that detects a light dispersed by the spectroscopic element and outputs a voltage signal.

* * * * *